US007994167B2

(12) United States Patent
Frank et al.

(10) Patent No.: US 7,994,167 B2
(45) Date of Patent: Aug. 9, 2011

(54) PENTAFLUOROSULPHANYL-SUBSTITUTED COMPOUND AND ITS USE FOR PRODUCING MEDICAMENTS

(75) Inventors: Robert Frank, Aachen (DE); Bernd Sundermann, Aachen (DE); Hans Schick, Berlin (DE)

(73) Assignee: Gruenenthal GmbH, Aachen (DE)

( * ) Notice: Subject to any disclaimer, the term of this patent is extended or adjusted under 35 U.S.C. 154(b) by 444 days.

(21) Appl. No.: 11/915,023

(22) PCT Filed: May 17, 2006

(86) PCT No.: PCT/EP2006/004658
§ 371 (c)(1),
(2), (4) Date: Jul. 8, 2008

(87) PCT Pub. No.: WO2006/122773
PCT Pub. Date: Nov. 23, 2006

(65) Prior Publication Data
US 2009/0137594 A1 May 28, 2009

(30) Foreign Application Priority Data
May 20, 2005 (DE) .......................... 10 2005 023 943

(51) Int. Cl.
*A61K 31/4965* (2006.01)
*A61K 31/497* (2006.01)
*C07D 401/04* (2006.01)
*C07D 487/00* (2006.01)
*C07D 403/00* (2006.01)
*C07D 239/02* (2006.01)
*C07D 241/02* (2006.01)
(52) U.S. Cl. .............. 514/248; 514/253.01; 514/255.05; 514/256; 544/236; 544/295; 544/326; 544/360; 544/409
(58) Field of Classification Search .............. 514/248, 514/256, 253.01, 255.05; 544/360, 236, 544/295, 326, 409
See application file for complete search history.

(56) References Cited

U.S. PATENT DOCUMENTS

| 3,073,861 A | 1/1963 | Raasch |
| 5,741,935 A | 4/1998 | Bowden et al. |
| 7,622,500 B2 * | 11/2009 | Gibson et al. ................. 514/469 |

FOREIGN PATENT DOCUMENTS

| EP | 1 627 869 A1 | 2/2006 |
| WO | WO 02/08221 A2 | 1/2002 |
| WO | WO 02/16318 A1 | 2/2002 |
| WO | WO 02/16319 A1 | 2/2002 |
| WO | WO 03/070247 A1 | 8/2003 |
| WO | WO 03/080578 A1 | 10/2003 |
| WO | WO 03/095420 A1 | 11/2003 |
| WO | WO 2004/024710 A1 | 3/2004 |
| WO | WO 2004/074290 A1 | 9/2004 |
| WO | WO 2004/089877 A1 | 10/2004 |
| WO | WO 2004/103954 A1 | 12/2004 |
| WO | WO 2004/108133 A2 | 12/2004 |
| WO | WO 2005/003084 A1 | 1/2005 |
| WO | WO 2005/007646 A1 | 1/2005 |
| WO | WO 2005/009977 A1 | 2/2005 |
| WO | WO 2005/009980 A1 | 2/2005 |
| WO | WO 2005/009987 A1 | 2/2005 |
| WO | WO 2005/016890 A1 | 2/2005 |
| WO | WO 2005/051390 | * 6/2005 |

OTHER PUBLICATIONS

Shin, et al., Bradykinin-12-lipoxygenase-VR1 Signaling Pathway for Inflammatory Hyperalgesia, Proceedings of the National Academy of Sciences of the United States of America, vol. 99, No. 15 (2002).*
Acs, et al., Trifluoperazine Modulates [3H]Resiniferatoxin Binding by Human and Rat Vanilloid (Capsaicin) Receptors and Affects 45Ca Uptake by Adult Rat Dorsal Root Ganglion Neurones, The J. of Pharmacology and Experimental Therapeutics, vol. 274, No. 3, 1090-1098 (1995).*
Park, H. et al., "*N*-4-Substituted-benzyl-*N'-tert*-butylbenzyl thioureas as vanilloid receptor ligands: investigation on the role of methanesulfonamido group in antagonistic activity", Bioorganic & Medicinal Chemistry Letters, 2004, vol. 14, pp. 787-791, Elsevier.
Ryu, C. H. et al., "Chain-branched 1,3-dibenzylthioureas as vanilloid receptor 1 antagonists", Bioorganic & Medicinal Chemistry Letters, 2004, vol. 14, pp. 1751-1755, Elsevier.
Park, H. et al., "Biarylcarboxybenzamide derivatives as potent vanilloid receptor (VR1) antagonistic ligands", Bioorganic & Medicinal Chemistry Letters, 2005, vol. 15, pp. 631-634, Elsevier.
Shao, B. et al., "4-(2-Pyridyl)piperazine-1-benzimidazoles as potent TRPV1 antagonistis", Bioorganic & Medicinal Chemistry Letters, 2005, vol. 15, pp. 719-723, Elsevier.
Bowden, R. D., "A New Method for the Synthesis of Aromatic Sulfurpentafluorides and Studies of the Stability of the Sulfurpentafluoride Group in Common Synthetic Transformations", Tetrahedron, 2000, vol. 56, pp. 3399-3408, Pergamon.
International Preliminary Report on Patentability including English translation (Seven (7) pages).
G. Ahern, Activation of TRPV1 by the Satiety Factor Oleoylethanolamide, The Journal of Biological Chemistry, vol. 278, No. 33, Aug. 15, pp. 30429-30434.
L.A. Birder et al., Altered urinary bladder function in mice lacking the vanilloid receptor TRPV1, Nature Neuroscience, vol. 5, No. 9, Sep. 2002, pp. 856-860.
M. Fu et al., TRPV1: A potential target for antiepileptogenesis, Medical Hypotheses 73 (2009), pp. 100-102.
J. Ghilardi et al., Selective Blockade of the Capasicin Receptor TRPV1 Attenuates Bone Cancer Pain, The Jounral of Neuroscience, Mar. 23, 2005, vol. 25, No. 12, pp. 3126-3131.
M. Gunthorpe et al., Characterization of SB-705498, a Potent and Selective Vanilloid Receptor-1 (VR1/TRPV1) Antagonist That Inhibits the Capsaicin-, Acid0, and Heat . . . , J. Pharmacology and Experimental Therapeutics, vol. 321, No. 3, pp. 1183-1192 (2007).

(Continued)

*Primary Examiner* — Andrew D Kosar
*Assistant Examiner* — Erich A Leeser
(74) *Attorney, Agent, or Firm* — Crowell & Moring LLP

(57) ABSTRACT

The present invention relates to pentafluorosulphanyl-substituted compounds, methods for their production, medicaments containing such compounds and the use of such compounds for producing medicaments.

22 Claims, No Drawings

OTHER PUBLICATIONS

P. Holzer, TRPV1 and the gut: from a tasty receptor for a painful vanilloid to a key player in hyperalgesia, *European Journal of Pharmacology 500*, 2004, pp. 231-241 (2004).

F. Leung, Capsaicin-sensitive intestinal mucosal afferent mechanism and body fat distribution, Life Sciences 83 (2008), pp. 1-5.

C. Maggi, Therapeutic Potential of Capsaicin-like Molecules: Studies in Animals and Humans, Life Sciences, vol. 51, pp. 1777-1781 (1992).

R. Marsch et a., Reduced Anxiety, Conditioned Fear, and Hippocampal Long-Term Potentiation in Transient Receptor Potential Vanilloid Type 1 Receptor-Deficient Mice, The Journal of Neuroscience, Jan. 24, 2007, vol. 27, No. 4, pp. 832-839.

V. Micale et al., Altered responses of dopamine D3 receptor null mice to excitotoxic or anxiogenic stimuli: Possible involvement of the endocannabinoid and endovanilloid systems, Neurobiology of Disease 36 (2009), pp. 70-80.

H. Pan et al., Sensing Tissue Ischemia: Another New Function for Capsaicin Receptors?, Circulation Journal of the American Heart Association, Circulation 2004, vol. 110, Issue 13, pp. 1826-1831.

R. Planells-Cases et al., Functional aspects and mechanisms of TRPV1 involvement in neurogenic inflammation that leads to thermal hyperalgesia, Pflugers Arch—Eur J. Physiol (2005) vol. 451, pp. 151-159.

H. Rami et al., The therapeutic potential of TRPV1 (VRI) antagonists: clinical answers await, Drug Discover Today: Therapeutic Strategies, vol. 1, No. 1, 2004, pp. 97-104.

H. Schultz, The spice of life is at the root of cardiac pain, Journal of Physiology (2003), 551.2, p. 400.

T. Sprenger et al., Migraine pathogenesis and state of pharmacological treatment options, BMC Medicine 2009, 7:71.

A. Suri et al., The emerging role of TRPV1 in diabetes and obesity, TRENDS in Pharmacological Sciences, vol. 29, No. 1, pp. 29-36 (2007).

* cited by examiner

PENTAFLUOROSULPHANYL-SUBSTITUTED COMPOUND AND ITS USE FOR PRODUCING MEDICAMENTS

The present invention relates to pentafluorosulphanyl-substituted compounds, methods for their production, medicaments containing these compounds and the use of these compounds for producing medicaments.

The treatment of pain, in particular neuropathic pain, is of great importance in medicine. There is a worldwide need for effective pain treatment. The urgent need for a treatment for chronic and non-chronic pain conditions that is both targeted and well suited to the patient, by which is meant a pain treatment that is both successful and satisfactory to the patient, is attested to by the large number of scientific works that have recently been published, both in the field of applied analgesia and in relation to basic research into nociception.

A suitable starting point for the treatment of pain, particularly neuropathic pain, is the vanilloid receptor of the subtype 1 (VR1/TRPV1), which is also often known as the capsaicin receptor. This receptor is stimulated inter alia by vanilloids, such as capsaicin, and by heat and by protons and plays a central part in the origination of pain. It is also responsible for a number of other physiological and pathophysiological processes, such as migraine, depression, neurodegenerative diseases, cognitive disorders, anxiety disorders, epilepsy, coughing, diarrhoea, pruritus, disturbances of the cardiovascular system, eating disorders, dependency on medications, medication abuse and, in particular, urinary incontinence.

It is an object of the present invention to provide new compounds which are suitable as pharmacological agents in medicaments for treating disorders or diseases that are at least partially mediated by vanilloid receptors 1 (VR1/TRPV1 receptors).

It has unexpectedly been found that pentafluorosulphanyl-substituted compounds of the general formula I are suitable for combating pain and have an excellent affinity for the vanilloid receptor of subtype 1 (VR1/TRPV1-receptor) and are therefore particularly suitable for the prophylaxis and/or treatment of disorders or illnesses that are at least partially mediated by vanilloid receptors 1 (VR1/TRPV1).

Pentafluorosulphanyl-substituted compounds of the general formula I therefore belong to the subject matter of the invention,

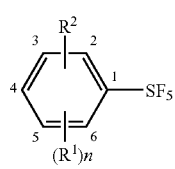

I wherein
n is 0, 1, 2, 3 or 4;
$R^1$ represents one or more mutually independent groups selected from the following: H, F, Cl, Br, I, —CN, —NC, —NO$_2$, —SO$_3$H, —S(=O$_2$)NH$_2$, —NH$_2$, —OH, —SH, methyl, ethyl, n-propyl, isopropyl, n-butyl, sec-butyl, isobutyl, tert-butyl, n-pentyl, sec-pentyl, n-hexyl, —O—CH$_3$, —O—C$_2$H$_5$, —O—CH(CH$_3$)$_2$, —O—C(CH$_3$)$_3$, —S—CH$_3$, —S—C$_2$H$_5$, —S—CH(CH$_3$)$_2$, —S—C(CH$_3$)$_3$, —N(CH$_3$)$_2$, —N(C$_2$H$_5$)$_2$, —NH—CH$_3$, —NH—C$_2$H$_5$, —NH—C(=O)—CH$_3$, —NH—C(=O)—C$_2$H$_5$, —C(=O)—NH$_2$, —C(=O)—CH$_3$, —C(=O)—C$_2$H$_5$, —C(=O)—OH, —C(=O)—OCH$_3$ and —C(=O)—OC$_2$H$_5$;

$R^2$ represents a group -A-B-D, -E-F or —N(H)-G, which can be bound to the 2-, 3-, 4-, 5- or 6-position of the phenyl group of the general formula I;
or a group -Q-B-D; wherein Q represents a group selected from the following: oxazolyl, thiazolyl, isoxazolyl, isothiazolyl and imidazolyl, which is condensed with the phenyl group of the general formula I and thereby forms a possibly substituted group selected from the following: benzoxazolyl, benzothiazolyl, benzisothiazolyl and benzimidazolyl;

A represents a group selected from the following: —N(R$^3$)—C(=O)—N(R$^4$)—, —N(R$^3$)—C(=S)—N(R$^4$)—, —N(R$^5$)—C(=O)—, —N(R$^5$)—C(=S)—,

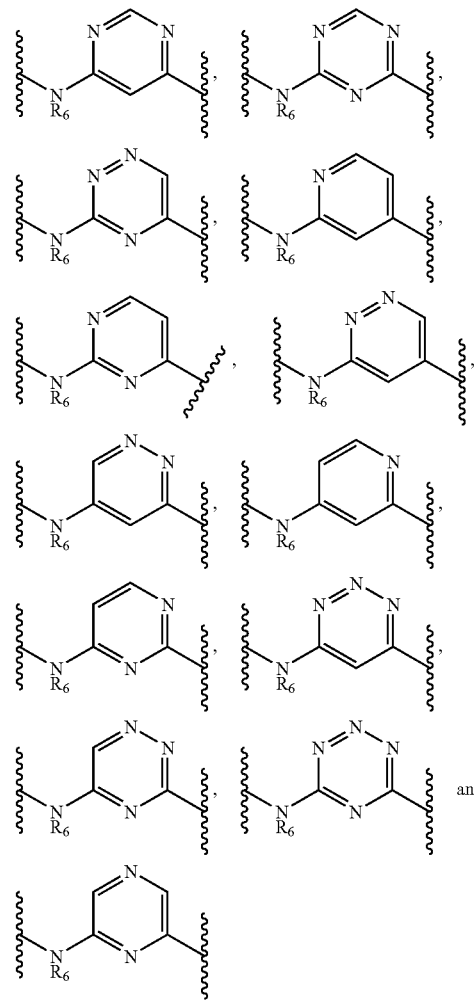

B represents a group selected from the following:

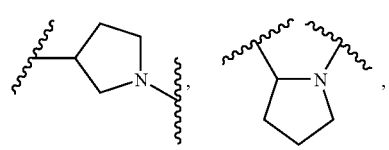

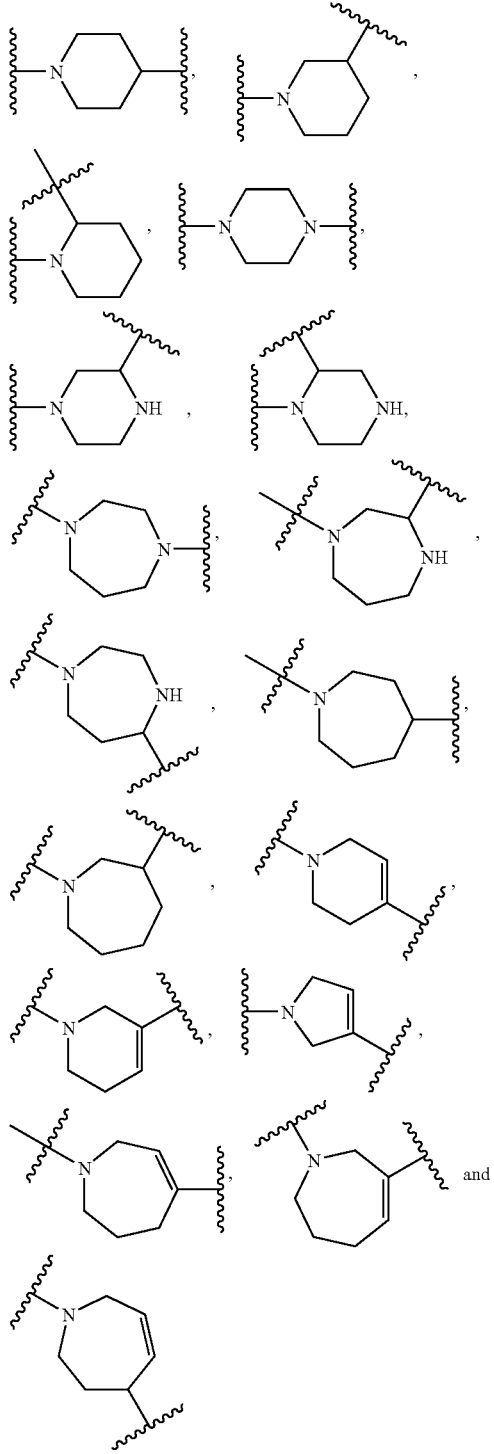

which may possibly be substituted with 1, 2, 3 or 4 substituents selected independently of one another from the following: methyl, ethyl, n-propyl, isopropyl, n-butyl, sec-butyl, isobutyl, tert-butyl, n-pentyl, sec-pentyl and n-hexyl;

or represents a phenylene group, which may be substituted with 1, 2, 3 or 4 substituents selected independently of one another from the following: F, Cl, Br, —CF₃, —OH, —O—CH₃, —O—C₂H₅, —O—CF₃, —O—CHF₂, —O—CF₂H, —S—CF₃, —S—CHF₂, —S—CF₂H, —NO₂, methyl, ethyl, n-propyl, isopropyl, n-butyl, sec-butyl, isobutyl and tert-butyl;

D represents a group selected from the following: phenyl, [1,3,5]-triazinyl, pyridinyl, pyridazinyl, pyrimidinyl, quinolinyl, isoquinolinyl and pyrazinyl, which may possibly be substituted with 1, 2, 3, 4 or 5 substituents selected independently of one another from the following: F, Cl, Br, —CF₃, —OH, —O—CH₃, —O—C₂H₅, —O—CF₃, —O—CHF₂, —O—CF₂H, —S—CF₃, —S—CHF₂, —S—CF₂H, —NO₂, methyl, ethyl, n-propyl, isopropyl, n-butyl, sec-butyl, isobutyl, tert-butyl, n-pentyl, sec-pentyl, n-hexyl, —NH—S(=O)₂—CH₃ and —NH—S(=O)₂—C₂H₅;

E represents a group selected from the following: —(CH₂)—(CH₂)—N(R⁷)—C(=O)—N(R⁸)—, —(CH₂)—(CH₂)—N(R⁷)—C(=S)—N(R⁸)—, —(CH₂)—N(R⁹)—C(=O)—N(R¹¹)—, —(CH₂)—N(R⁹)—C(=S)—N(R¹⁰)—, —CH=CH—C(=O)—N(R¹¹)—, —CH=CH—C(=S)—N(R¹¹)—, —(CH₂)—(CH₂)—N(R¹²)—C(=O)—N(R¹³)—(CH₂)—(CH₂)—, —(CH₂)—(CH₂)—N(R¹²)—C(=S)—N(R¹³)—(CH₂)—(CH₂)—, —(CH₂)—N(R¹⁴)—C(=O)—N(R¹⁵)—(CH₂)—, —(CH₂)—N(R¹⁴)—C(=S)—N(R¹⁵)—(CH₂)—, —N(R¹⁶)—C(=O)—N(R¹⁷)—, —N(R¹⁶)—C(=S)—N(R¹⁷)—, —(CH₂)—N(R¹⁸)—C(=O)—CH(CH₃)—, —(CH₂)—N(R¹⁸)—C(=S)—CH(CH₃)—, —C(=O)—N(R¹⁹)—(CH₂)—, —C(=S)—N(R¹⁹)—(CH₂)—, —N(R²⁰)—(CH₂)—C(=O)—N(R²¹)—, —N(R²⁰)—(CH₂)—C(=S)—N(R²¹), —(CH₂)—(CH₂)—N(R²²)—C(=O)—, —(CH₂)—(CH₂)—N(R²²)—C(=S)—, —CH(CH₃)—N(R²³)—C(=O)—, —CH(CH₃)—N(R²³)—C(=S)—, —(CH₂)—N(R²⁴)—C(=O)—N(R²⁵)—CH(CH₃)— and —(CH₂)—N(R²⁴)—C(=S)—N(R²⁵)—CH(CH₃)—;

F represents a group selected from the following: phenyl, naphthyl, quinolinyl, isoquinolinyl, quinoxalinyl, quinazolinyl, (1,4)-benzodioxanyl, (1,3)-benzdioxolyl, (1,2,3,4)-tetrahydronaphthyl, (1,2,3,4)-tetrahydroquinolinyl, (1,2,3,4)-tetrahydroisoquinolinyl, benzoxazolyl, benzothiazolyl, benzisoxazolyl, benzisothiazolyl, benzimidazolyl, 2-oxo-2,3-dihydro-1H-benzimidazolyl, 2-benzoxazolinonyl and 2-benzothiazolinonyl, which may possibly be substituted with 1, 2, 3, 4 or 5 substituents selected independently of one another from the following: F, Cl, Br, —CF₃, —OH, —O—CH₃, —O—C₂H₅, —O—CF₃, —O—CHF₂, —O—CF₂H, —S—CF₃, —S—CHF₂, —S—CF₂H, —NO₂, methyl, ethyl, n-propyl, isopropyl, n-butyl, sec-butyl, isobutyl, tert-butyl, n-pentyl, sec-pentyl, n-hexyl, —NH—S(=O)₂—CH₃ and —NH—S(=O)₂—C₂H₅;

G represents a group selected from the following:

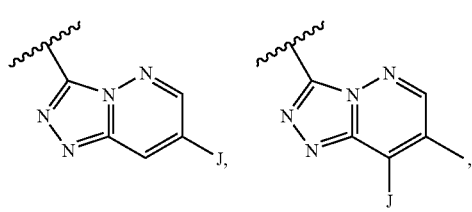

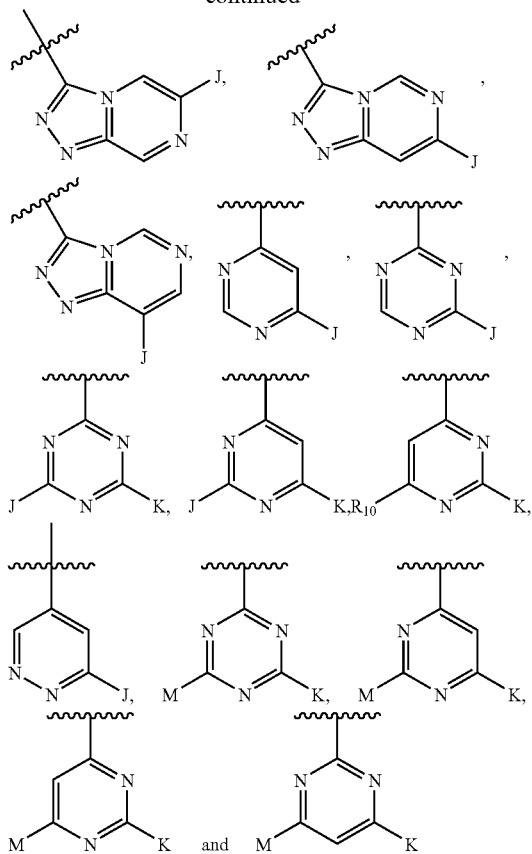

J represents a group selected from the following: phenyl, [1,3,5]-triazinyl, pyridinyl, pyridazinyl, pyrimidinyl, quinolinyl, isoquinolinyl and pyrazinyl, which may possibly be substituted with 1, 2, 3, 4 or 5 substituents selected independently of one another from the following: F, Cl, Br, —CF$_3$, —OH, —O—CH$_3$, —O—C$_2$H$_5$, —O—CF$_3$, —O—CHF$_2$, —O—CF$_2$H, —S—CF$_3$, —S—CHF$_2$, —S—CF$_2$H, —NO$_2$, methyl, ethyl, n-propyl, isopropyl, n-butyl, sec-butyl, isobutyl, tert-butyl, n-pentyl, sec-pentyl, n-hexyl, —NH—S(=O)$_2$—CH$_3$ and —NH—S(=O)$_2$—C$_2$H$_5$;

K represents a group selected from the following: piperidinyl, piperazinyl, pyrrolidinyl, morpholinyl, thiomorpholinyl, (1,2,3,6)-tetrahydropyridinyl, cyclohexyl, cyclopentyl, cycloheptyl, azepanyl and diazepanyl, which may be substituted with 1, 2, 3 or 4 substituents selected independently of one another from the following: methyl, ethyl, n-propyl, isopropyl, n-butyl, sec-butyl, isobutyl, tert-butyl, n-pentyl, sec-pentyl, n-hexyl, —NH—CH$_3$, —NH—C$_2$H$_5$, —N(CH$_3$)$_2$ and —N(C$_2$H$_5$);
or represents a —NR$^{26}$R$^{27}$-group;

M represents a phenyl group, which may be substituted with 1, 2, 3, 4 or 5 substituents selected independently of one another from the following: —SF$_5$, F, Cl, Br, —CF$_3$, —OH, —O—CH$_3$, —O—C$_2$H$_5$, —O—CF$_3$, —O—CHF$_2$, —O—CF$_2$H, —S—CF$_3$, —S—CHF$_2$, —S—CF$_2$H, —NO$_2$, methyl, ethyl, n-propyl, isopropyl, n-butyl, sec-butyl, isobutyl and tert-butyl and/or can be bound via a —O—CH$_2$—, —S—CH$_2$—, —CH$_2$—CH$_2$—, —CH=CH— or —CH$_2$-group;

R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$, R$^{23}$, R$^{24}$ and R$^{25}$ represent, independently of one another, a hydrogen group
or a group selected from the following: hydrogen, methyl, ethyl, n-propyl, isopropyl, n-butyl, sec-butyl, isobutyl, tert-butyl, n-pentyl, sec-pentyl and n-hexyl; and R$^{26}$ and R$^{27}$ represent, independently of one another,
a group selected from the following: hydrogen, methyl, ethyl, n-propyl, isopropyl, n-butyl, sec-butyl, isobutyl, tert-butyl, n-pentyl, sec-pentyl and n-hexyl;

each possibly in the form of its pure stereoisomers, in particular enantiomers or diastereoisomers, its racemates or in the form of a mixture of stereoisomers, in particular enantiomers and/or diastereoisomers in any desired mixing ratio or in the form of corresponding salts, or respectively in the form of corresponding solvates.

Particularly preferable are pentafluorosulphanyl-substituted compounds of the above general formula I, wherein
n is 0,
R$^2$ represents a group -A-B-D, -E-F or —N(H)-G, which is bound to position 4 of the phenyl group of the general formula I,
or a group -Q-B-D; wherein Q represents a group selected from the following: oxazolyl, thiazolyl, isoxazolyl, isothiazolyl and imidazolyl, which is condensed with the phenyl group of the general formula I in positions 4 and 5 and therefore forms a possibly substituted group selected from the following: benzoxazolyl, benzothiazolyl, benzisothiazolyl and benzimidazolyl, A represents a group selected from the following: —N(R$^3$)—C(=O)—N(R$^4$)—, —N(R$^3$)—C(=S)—N(R$^4$)—, —N(R$^5$)—C(=O)—, —N(R$^5$)—C(=S)—,

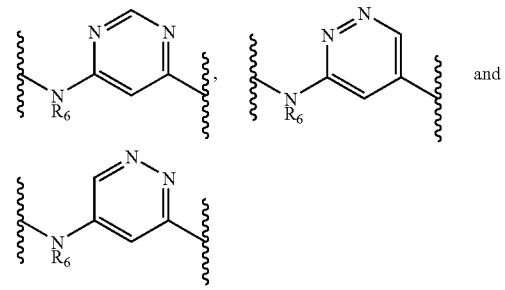

B represents a group selected from the following:

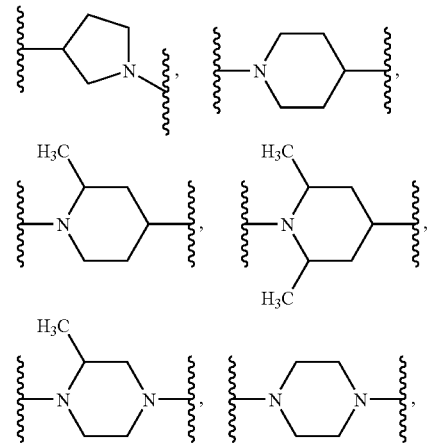

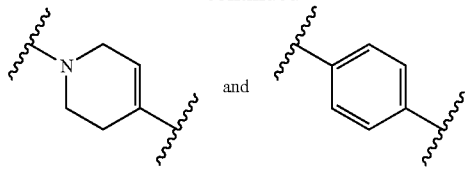

D represents a group selected from the following:

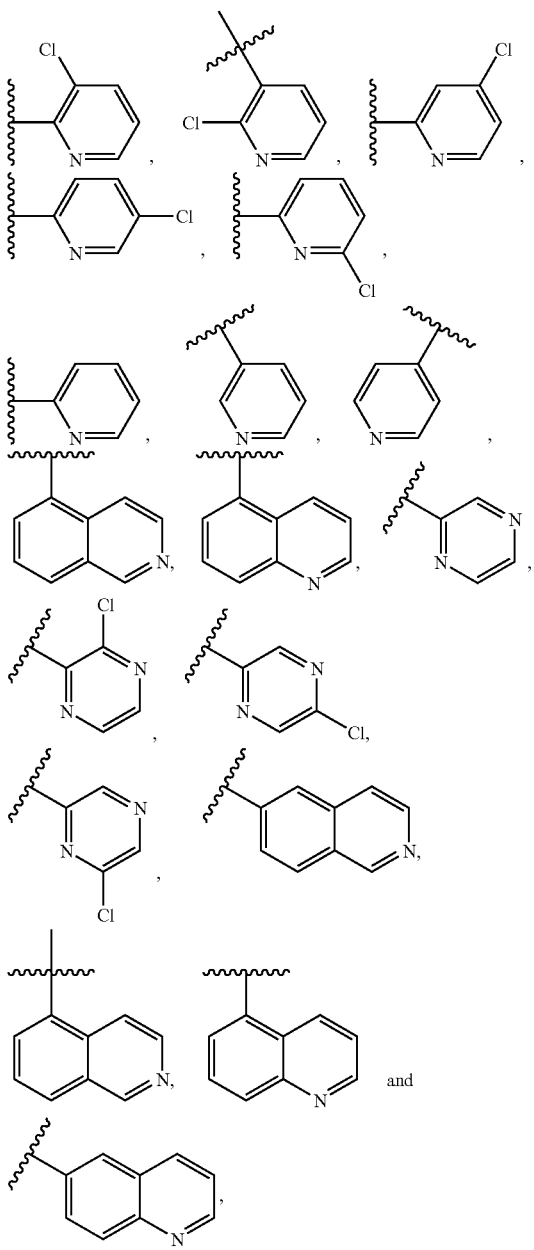

E represents a group selected from the following: —(CH$_2$)—(CH$_2$)—N(R$^7$)—C(=O)—N(R$^8$)—, —(CH$_2$)—(CH$_2$)—N(R$^7$)—C(=S)—N(R$^8$)—, —(CH$_2$)—N(R$^9$)—C(=O)—N(R$^{10}$)—, —(CH$_2$)—N(R$^9$)—C(=S)—N(R$^{10}$)—, —CH=CH—C(=O)—N(R$^{11}$)—, —CH=CH—C(=S)—N(R$^{11}$)—, —(CH$_2$)—(CH$_2$)—N(R$^{12}$)—C(=O)—N(R$^{13}$)—(CH$_2$)—(CH$_2$)—, —(CH$_2$)—N(R$^{12}$)—C(=S)—N(R$^{13}$)—(CH$_2$)—(CH$_2$)—, —(CH$_2$)—N((R$^{14}$))C(=O)—N(R$^{15}$)—(CH$_2$)—, —(CH$_2$)—N(R$^{14}$)—C(=S)—N(R$^{15}$)—(CH$_2$)—, —N(R$^{16}$)—C(=O)—N(R$^{17}$)—, —N(R$^{16}$)—C(=S)—N(R$^{17}$)—, —(CH$_2$)—N(R$^{18}$)—C(=O)—CH(CH$_3$)—, —(CH$_2$)—N(R$^{18}$)—C(=S)—CH(CH$_3$)—, —C(=O)—N(R$^{19}$)—(CH$_2$)—, —C(=S)—N(R$^{19}$)—(CH$_2$)—, —N(R$^{20}$)—(CH$_2$)—C(=O)—N(R$^{21}$)—, —N(R$^{20}$)—(CH$_2$)—C(=S)—N(R$^{21}$)—, —(CH$_2$)—(CH$_2$)—N(R$^{22}$)—C(=O)—, —(CH$_2$)—(CH$_2$)—N(R$^{22}$)—C(=S)—, —CH(CH$_3$)—N(R$^{23}$)—C(=O)—, —CH(CH$_3$)—N(R$^{23}$)—C(=S)—, —(CH$_2$)—N(R$^{24}$)—C(=O)—N(R$^{25}$)—CH(CH$_3$)— and —(CH$_2$)—N(R$^{24}$)—C(=S)—N(R$^{25}$)—CH(CH$_3$)—;

F represents a group selected from the following:

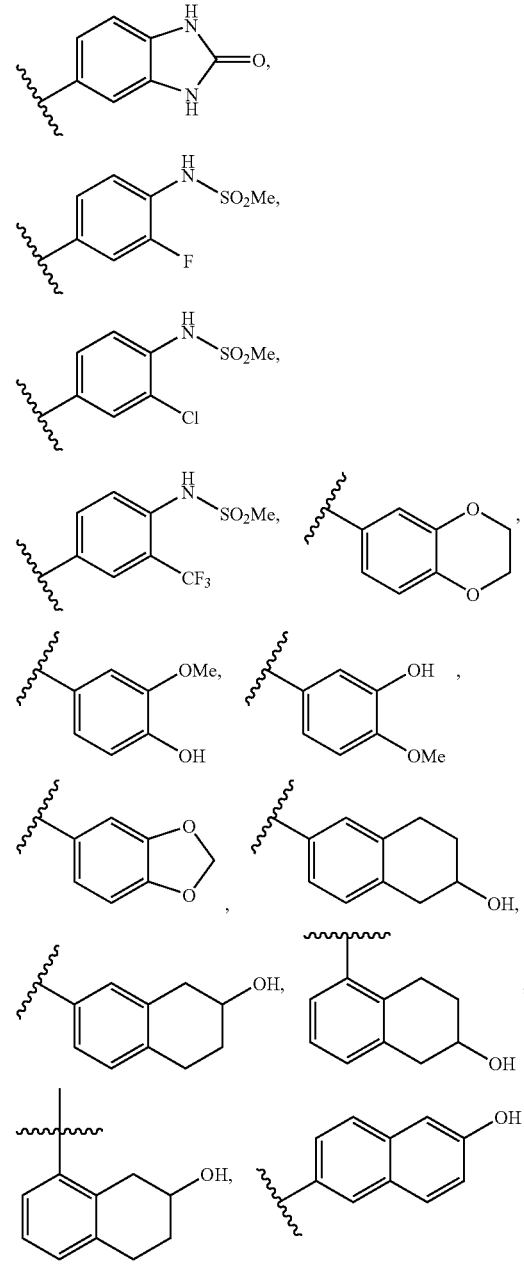

-continued
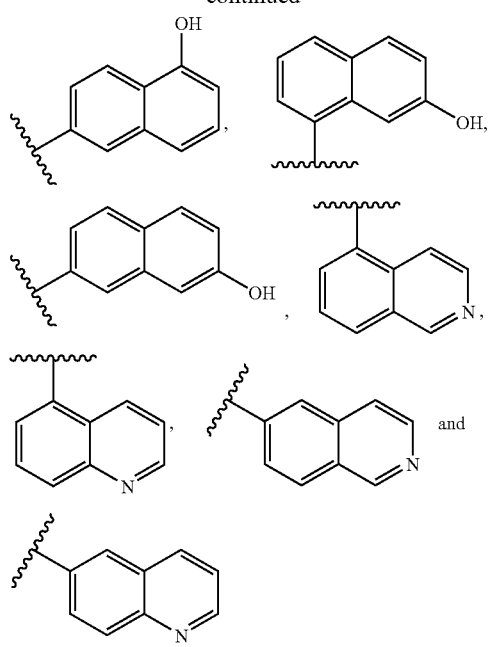
G represents a group selected from the following:
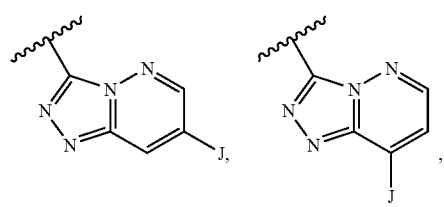
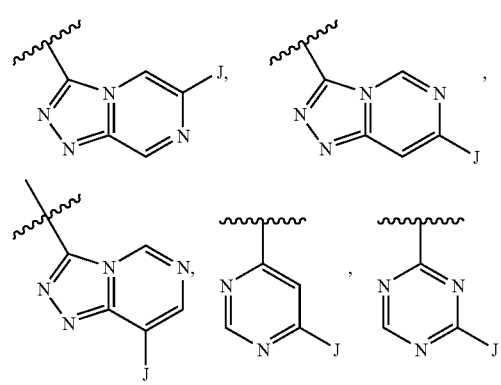
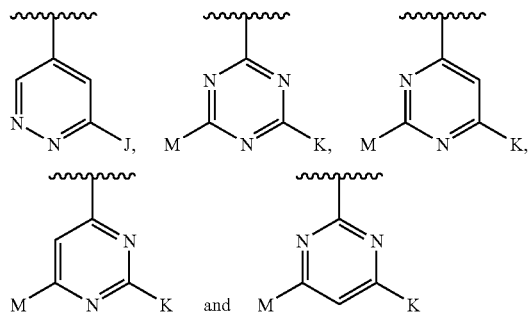
J represents a group selected from the following:
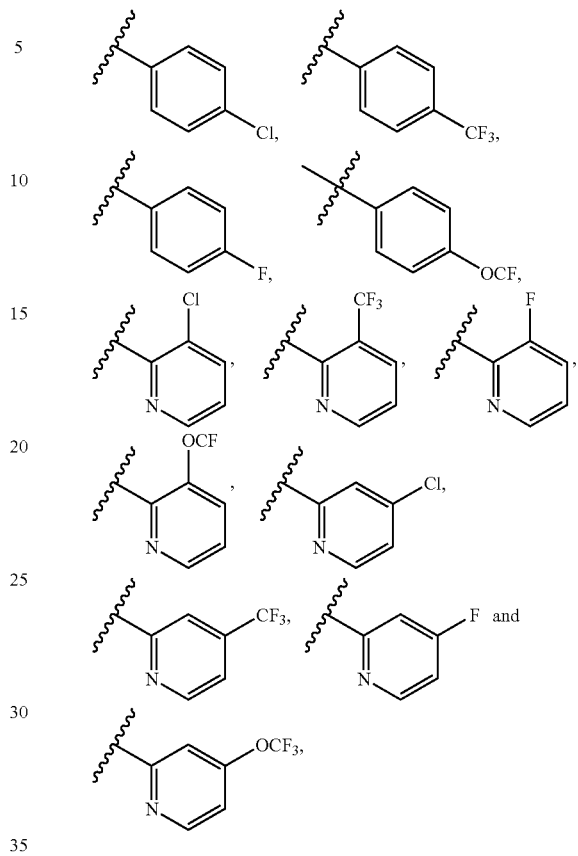
K represents a group selected from the following:
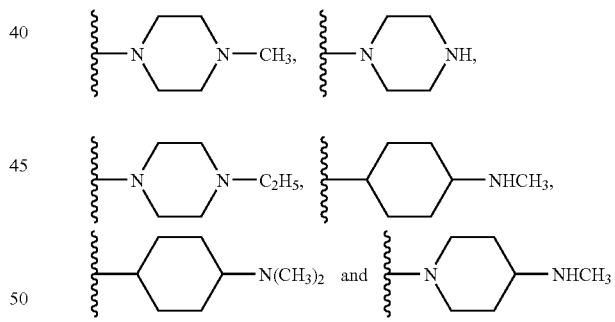
M represents a group selected from the following:
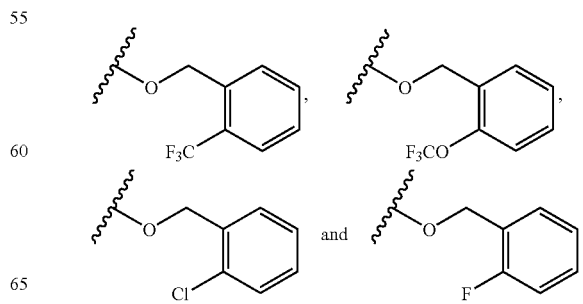

and $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$ and $R^{25}$ each represent a hydrogen group;

each possibly in the form of its pure stereoisomers, in particular enantiomers or diastereoisomers, its racemates or in the form of a mixture of stereoisomers, in particular enantiomers and/or diastereoisomers in any desired mixing ratio or in the form of corresponding salts, or respectively in the form of corresponding solvates.

Especially preferable are pentafluorosulphanyl-substituted compounds of the general formula I selected from the following:

[1] N-{4-[3-(4-pentafluorosulphanyl-benzyl)-thioureidomethyl]-2-fluoro-phenyl}-methane sulphonamide

[2] 4-(3-chloropyridin-2-yl)-piperazine-1-carboxy-(4-pentafluorosulphanyl-phenyl)-amide

[3] 4-(3-chloro-pyridin-2-yl)-piperazine-1-thiocarboxy-(4-pentafluorosulphanyl-phenyl)-amide

[4] 3-(4-pentafluorosulphanyl-phenyl)-N-(2,3-dihydrobenzo[1,4]dioxin-6-yl)-acrylamide

[5] N-(4-pentafluorosulphanyl-benzyl)-2-(3-fluoro-4-methanesulphonylamino-phenyl)-propionamide

[6] (2R)—N-(4-pentafluorosulphanyl-benzyl)-2-(3-fluoro-4-methansulphonylamino-phenyl)-propionamide

[7] (2S)—N-(4-pentafluorosulphanyl-benzyl)-2-(3-fluoro-4-methanesulphonylamino-phenyl)-propionamide

[8] N-(4-pentafluorosulphanyl-phenyl)-4-pyridin-2-yl-benzamide

[9] 1-(4-pentafluorosulphanyl-benzyl)-3-(7-hydroxy-naphthalen-1-yl)-urea

[10] 4-(3-chloro-pyrazin-2-yl)-3,6-dihydro-2H-pyridine-1-carboxy-(4-pentafluorosulphanyl-phenyl)-amide

[1,1] (4-pentafluorosulphanyl-phenyl)-[4-(4-methyl-piperazin-1-yl)-6-(2-trifluoromethyl-benzyloxy)-[1,3,5]triazin-2-yl]-amine

[12] (4-pentafluorosulphanyll-phenyl)-[6-(4-chloro-phenyl)-pyrimidin-4-yl]-amine

[13] 4-pentafluorosulphanyl-N-(2-oxo-2,3-dihydro-1H-benzoimidazol-5-ylmethyl)-benzamide

[14] (4-pentafluorosulphanyl-phenyl)-{6-[4-(3-chloro-pyridin-2-yl)-2-(R)-methyl-piperazin-1-yl]-pyrimidin-4-yl}-amine

[15] 3'-chloro-3,6-dihydro-2H-[1,2']bipyridinyl-4-carboxy-(4-pentafluorosulphanyl-phenyl)-amide

[16] 2-(4-pentafluorosulphanyl-phenylamino)-N-(7-hydroxy-naphthalen-1-yl)-acetamide

[17] (4-pentafluorosulphanyl-phenyl)-[7-(3-trifluoromethylpyridin-2-yl)-[1,2,4]triazolo[4,3-b]pyridazin-3-yl]-amine

[18] 1-(4-pentafluorosulphanyl-benzyl)-3-isoquinolin-5-yl-urea

[19] 1-[2-(4-pentafluorosulphanyl-phenyl)-ethyl]-3-isoquinolin-5-yl-urea

[20] 1-(4-pentafluorosulphanyl-phenyl)-3-(7-hydroxy-5,6,7,8-tetrahydro-naphthalen-1-yl)-urea

[21] 1-[2-(4-pentafluorosulphanyl-phenyl)-ethyl]-3-quinolin-5-yl-urea

[22] 1-(4-pentafluorosulphanyl-phenyl)-3-(1-isoquinolin-5-yl-pyrrolidin-3-yl)-urea

[23] 5-pentafluorosulphanyl-2-[4-(3-chloro-pyridin-2-yl)-piperazin-1-yl]-benzooxazole and

[24] N-{4-[3-(4-pentafluorosulphanyl-benzyl)-ureidomethyl]-2-fluoro-phenyl}-methanesulphonamide.

In addition, compounds according to the invention may be preferable which, in a FLIPR assay at a concentration of 10 μM, show inhibition of the $Ca^{2+}$ ion inflow in dorsal root ganglia of rats of at least 10%, preferably at least 30%, particularly preferably at least 50%, especially preferably at least 70% and still more preferably at least 90% compared with the maximum achievable inhibition of the $Ca^{2+}$ cation inflow with capsaicin at a concentration of 10 μM.

In the FLIPR assay, the $Ca^{2+}$ inflow can be quantified with the aid of a $Ca^{2+}$-sensitive dye (of the type Fluo-4, from Molecular Probes Europe BV, Leiden, Netherlands) in a Fluorescent Imaging Plate Reader (FLIPR, from Molecular Devices, Sunnyvale, USA), as described below.

The compounds according to the invention are characterised by their good metabolic stability, which is due to the pentafluorosulphanyl-group. This group is unexpectedly more slowly decomposed compared with sterically comparable groups such as a tert-butyl group.

The relevant structural formulae of the compounds [1]-[24] are given in the following scheme 1.

Scheme 1.

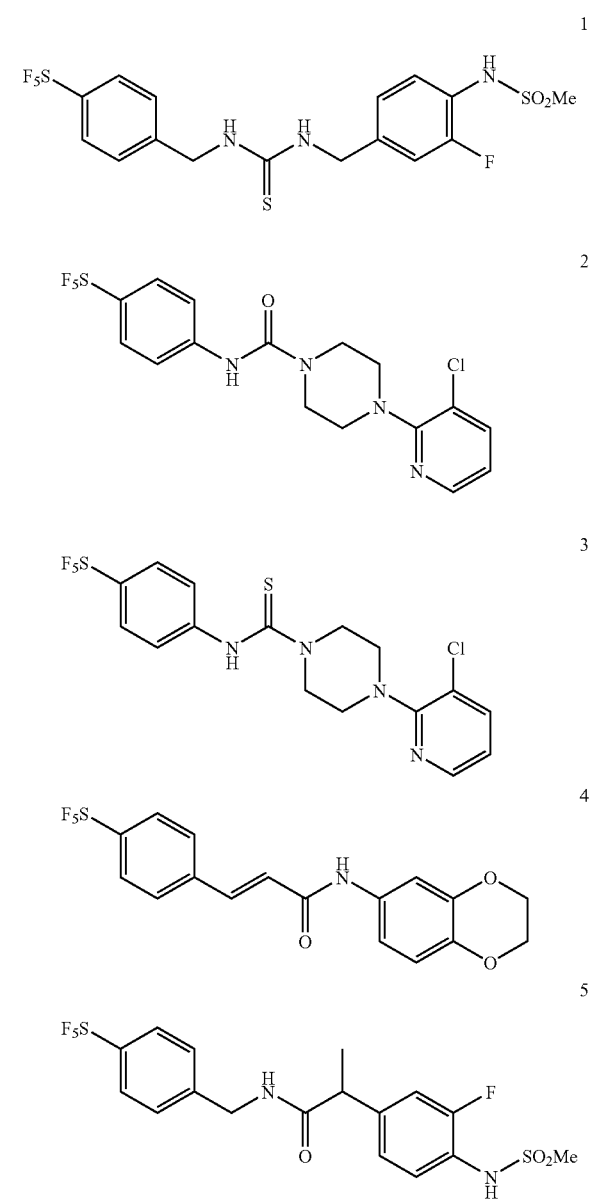

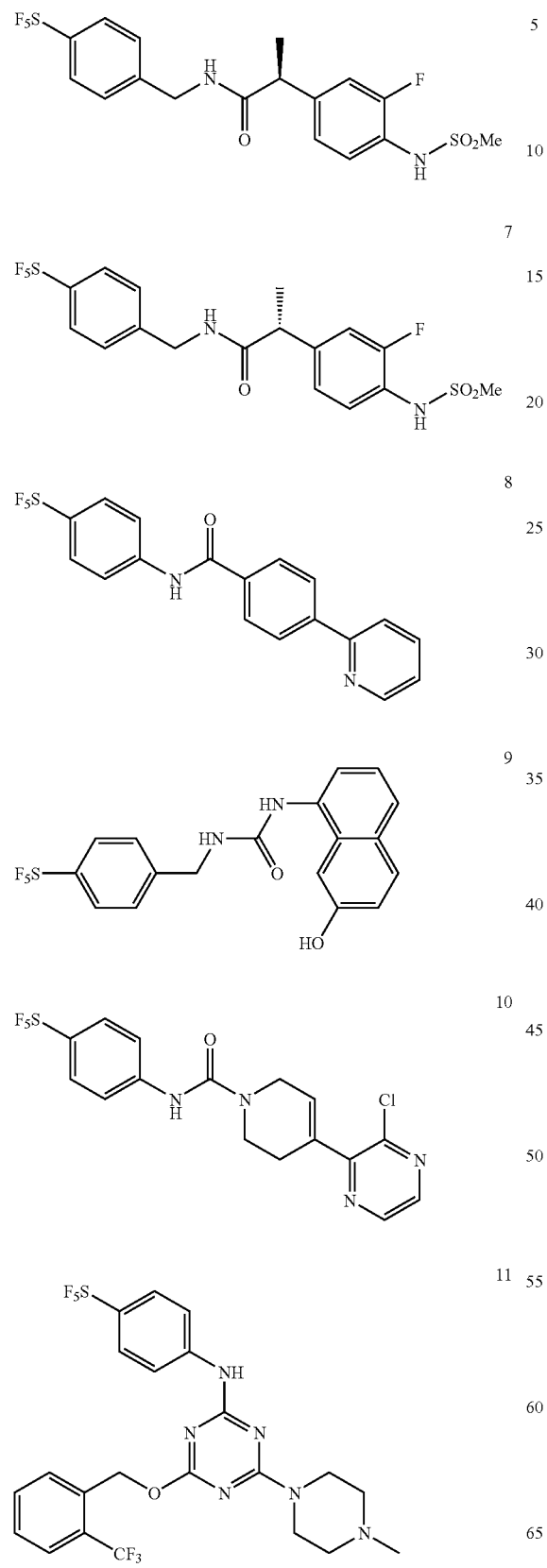
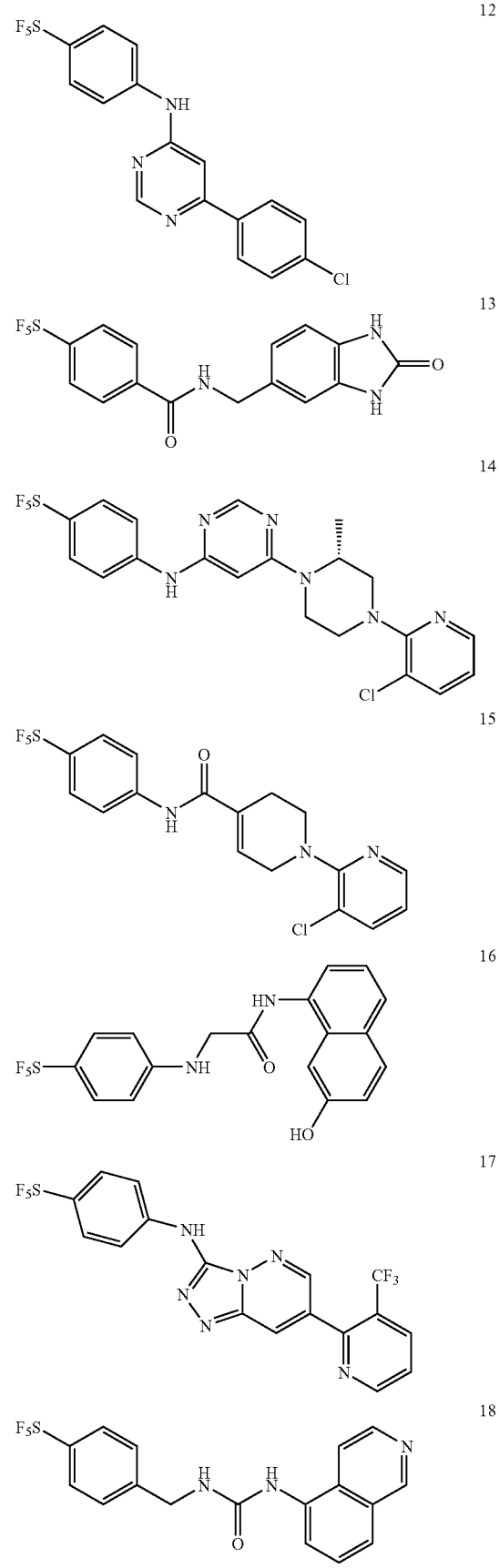

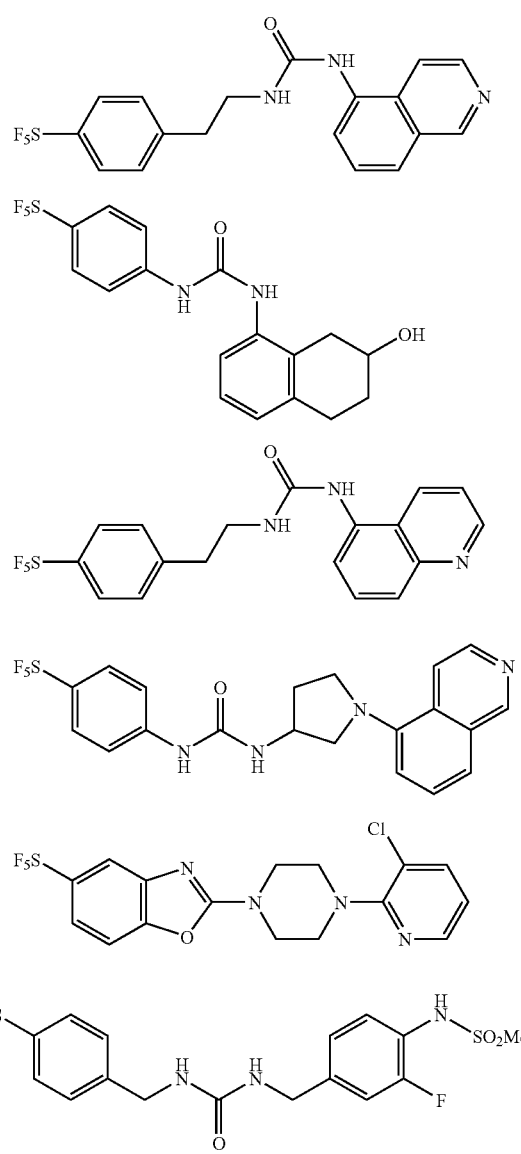

Also the subject matter of the present invention is a method for producing compounds of the general formula I, according to which at least one compound of the general formula II,

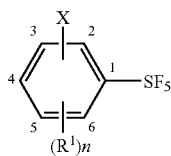

II wherein $R^1$ and n denote the same as above and X represents —N=C=O, —N=C=S, —(CH$_2$)—N=C=O, —(CH$_2$)—N=C=S, —(CH$_2$)—N=C=S, —(CH$_2$)—(CH$_2$)—N=C=O, —(CH$_2$)—(CH$_2$)—N=C=S, —CH(CH$_3$)—N=C=O or —CH(CH$_3$)—N=C=S, is reacted in a reaction medium, preferably in a reaction medium selected from the following: dimethylformamide, toluene, acetonitrile, dichloromethane, diethyl ether, tetrahydrofuran and dimethyl sulphoxide, in the presence of at least one base, preferably in the presence of at least one organic base selected from the following: triethylamine, diisopropylethylamine, N-methylmorpholine, pyridine and dimethylaminopyridine, with at least one compound of the general formula H—B-D; wherein the group H—B has at least one —N(H)-group, H$_2$N—B-D, H$_2$N—F, H$_2$N—(CH$_2$)—F, H$_2$N—(CH$_2$)—(CH$_2$)—F or H$_2$N—CH(CH$_3$)—F; wherein B, D and F denote the same as above;

or at least one compound of the general formula II, wherein $R^1$ and n denote the same as above and X represents —NH$_2$, —(CH$_2$)—NH$_2$, —CH(CH$_3$)—NH$_2$ or —(CH$_2$)—(CH$_2$)—NH$_2$, is reacted in a reaction medium, preferably in a reaction medium selected from the following: dimethylformamide, toluene, acetonitrile, dichloromethane, diethyl ether, tetrahydrofuran and dimethyl sulphoxide, in the presence of at least one base, preferably in the presence of an organic base selected from the following: triethylamine, diisopropylethylamine, N-methylmorpholine, pyridine and dimethylaminopyridine, with at least one compound of the general formula F—N=C=O, F—N=C=S, F—(CH$_2$)—N=C=O, F—(CH$_2$)—N=C=S, F—(CH$_2$)—(CH$_2$)—N=C=O, F—(CH$_2$)—(CH$_2$)—N=C=S, F—CH(CH$_3$)—N=C=O or F—CH(CH$_3$)—N=C=S; wherein F denotes the same as above;

and is converted to at least one compound of the general formula I; wherein $R^1$ and n denote the same as above and $R^2$ represents -A-B-D or -E-F, wherein A represents —N($R^3$)—C(=O)—N($R^4$)— or —N($R^3$)—C(=S)—N($R^4$)—; E represents a group selected from the following: —(CH$_2$)—(CH$_2$)—N($R^7$)—C(=O)—N($R^8$)—, —(CH$_2$)—(CH$_2$)—N($R^7$)—C(=S)—N($R^8$)—, —(CH$_2$)—N($R^9$)—C(=O)—N($R^{10}$)—, —(CH$_2$)—N($R^9$)—C(=S)—N($R^{10}$)—, —(CH$_2$)—(CH$_2$)—N($R^{12}$)—C(=O)—N($R^{13}$)—(CH$_2$)—(CH$_2$)—, —(CH$_2$)—(CH$_2$)—N($R^{12}$)—C(=S)—N($R^{13}$)—(CH$_2$)—(CH$_2$)—, —(CH$_2$)—N($R^{14}$)—C(=O)—N($R^{15}$)—(CH$_2$)—, —(CH$_2$)—N($R^{14}$)—C(=S)—N($R^{15}$)—(CH$_2$)—, —N($R^{16}$)—C(=O)—N($R^{17}$), —N($R^{16}$)—C(=S)—N($R^{17}$)—, —(CH$_2$)—N($R^{24}$)—C(=O)—N($R^{25}$)—CH(CH$_3$)— and —(CH$_2$)—N($R^{24}$)—C(=S)—N($R^{25}$)—CH(CH$_3$)—; wherein $R^3$, $R^4$, $R^7$, $R^8$, $R^9$, $R^{10}$, $R^{12}$, $R^{13}$, $R^{14}$, $R^{15}$, $R^{16}$, $R^{17}$, $R^{24}$ and $R^{25}$ each represent hydrogen; and B, D and F denote the same as above; and this compound is possibly purified and/or isolated, and possibly at least one compound of the general formula I; wherein $R^1$ and n denote the same as above and $R^2$ represents -A-B-D or -E-F, wherein A represents —N($R^3$)—C(=O)—N($R^4$)— or —N($R^3$)—C(=S)—N($R^4$)—; E represents a group selected from the following: —(CH$_2$)—(CH$_2$)—N($R^7$)—C(=O)—N($R^8$)—, —(CH$_2$)—(CH$_2$)—N($R^7$)—C(=S)—N($R^8$)—, —(CH$_2$)—N($R^9$)—C(=O)—N($R^{10}$)—, —(CH$_2$)—N($R^9$)—C(=S)—N($R^{10}$)—, —(CH$_2$)—(CH$_2$)—N($R^{12}$)—C(=O)—N($R^{13}$)—(CH$_2$)—(CH$_2$)—, —(CH$_2$)—(CH$_2$)—N($R^{12}$)—C(=S)—N($R^{13}$)—(CH$_2$)—(CH$_2$)—, —(CH$_2$)—N($R^{14}$)—C(=O)—N($R^{15}$)—(CH$_2$)—, —(CH$_2$)—N($R^{14}$)—C(=S)—N($R^{15}$)—(CH$_2$)—, —N($R^{16}$)—C(=O)—N($R^{17}$), —N($R^{16}$)—C(=S)—N($R^{17}$)—, —(CH$_2$)—N($R^{24}$)—C(=O)—N($R^{25}$)—CH(CH$_3$)— and —(CH$_2$)—N($R^{24}$)—C(=S)—N($R^{25}$)—CH(CH$_3$)—; wherein $R^3$, $R^4$, $R^7$, $R^8$, $R^9$, $R^{10}$, $R^{12}$, $R^{13}$, $R^{14}$, $R^{15}$, $R^{16}$, $R^{17}$, $R^{24}$ and $R^{25}$ each represent hydrogen; and B, D and F denote the same as above; is reacted in a reaction medium, preferably in a reaction medium selected from the following: dimethylformamide, toluene, acetonitrile, dichloromethane, diethyl ether, tetrahydrofuran and dimethyl sulphoxide, in the presence of a base, preferably in the presence of a metal hydride salt, particularly preferably in the presence of potassium hydride and/or sodium hydride, with at least one compound of the general formula LG-R³, LG-R⁴, LG-R⁷, LG-R⁸, LG-R⁹, LG-R¹⁰, LG-R¹², LG-R¹³, LG-R¹⁴, LG-R¹⁵, LG-R¹⁶, LG-R¹⁷, LG-R²⁴ or LG-R²⁵; wherein R³, R⁴, R⁷, R⁸, R⁹, R¹⁰, R¹², R¹³, R¹⁴, R¹⁵, R¹⁶, R¹⁷, R²⁴ and R²⁵ denote the same as above with the exception of hydrogen and LG denotes a leaving group, preferably a halogen atom, particularly preferably a chlorine atom, and is converted to at least one compound of the general formula i, wherein R¹ and n denote the same as above and R² represents -A-B-D or -E-F, wherein A represents —N(R³)—C(=O)—N(R⁴)— or —N(R³)—C(=S)—N(R⁴)—; E represents a group selected from the following: —(CH₂)—(CH₂)—N(R⁷)—C(=O)—N(R⁸)—, —(CH₂)—(CH₂)—N(R⁷)—C(=S)—N(R⁸)—, —(CH₂)—N(R⁹)—C(=O)—N(R¹⁰)—, —(CH₂)—N(R⁹)—C(=S)—N(R¹⁰)—, —(CH₂)—(CH₂)—N(R¹²)—C(=O)—N(R¹³)—(CH₂)—(CH₂)—, —(CH₂)—(CH₂)—N(R¹²)—C(=S)—N(R¹³)—(CH₂)—(CH₂)—, —(CH₂)—N(R¹⁴)—C(=O)—N(R¹⁵)—(CH₂)—, —(CH₂)—N(R¹⁴)—C(=S)—N(R¹⁵)—(CH₂)—, —N(R¹⁶)—C(=O)—N(R¹⁷)—, —N(R¹⁶)—C(=S)—N(R¹⁷)—, —(CH₂)—N(R²⁴)—C(=O)—N(R²⁵)—CH(CH₃)— and —(CH₂)—N(R²⁴)—C(=S)—N(R²⁵)—CH(CH₃)—; wherein R³, R⁴, R⁷, R⁸, R⁹, R¹⁰, R¹², R¹³, R¹⁴, R¹⁵, R¹⁶, R¹⁷, R²⁴ and R²⁵ each denote the same as above with the exception of hydrogen; and B, D and F denote the same as in one or more of the claims 1 to 12;

and this compound is possibly purified and/or isolated.

Also the subject matter of the present invention is a method for producing compounds of the general formula I according to which at least one compound of the general formula II,

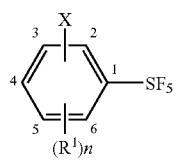

II wherein R¹ and n denote the same as above and X represents —NH₂, is reacted in a reaction medium selected from the following: dimethylformamide, xylene, mesitylene, toluene, acetonitrile, dichloromethane, diethyl ether, tetrahydrofuran and dimethyl sulphoxide, with at least one compound with the formula LG-G, wherein G denotes the same as above and LG denotes a leaving group, preferably a halogen atom and particularly preferably a fluorine atom or a chlorine atom, and is converted to at least one compound of the general formula I, wherein R¹ and n denote the same as above and R² represents —N(H)-G, wherein G denotes the same as above, and this compound is possibly purified and/or isolated.

Also the subject matter of the present invention is a method for producing compounds of the general formula I, according to which at least one compound of the general formula III,

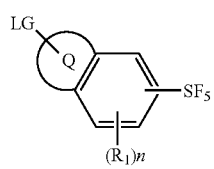

III wherein R¹, n and Q denote the same as above and LG denotes a leaving group, preferably a halogen atom and particularly preferably a fluorine atom or a chlorine atom, is reacted in a reaction medium, preferably a reaction medium selected from the following: dimethylformamide, xylene, mesitylene, toluene, acetonitrile, dichloromethane, diethyl ether, tetrahydrofuran and dimethyl sulphoxide, with at least one compound of the general formula H—B-D; wherein the group H—B has at least one —N(H)— group and B and D denote the same as above, and is converted to at least one compound of the general formula I, wherein R¹ and n denote the same as above and R² represents -Q-B-D, wherein Q, B and D denote the same as above, and this compound is possibly purified and/or isolated.

Also the subject matter of the present invention is a method for producing compounds of the general formula I according to which at least one compound of the general formula II,

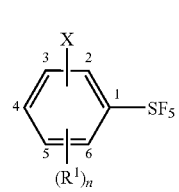

II wherein R¹ and n denote the same as above and X represents —C(=O)-LG, —(CH₂)—C(=O)-LG, —(CH₂)—(CH₂)—C(=O)-LG, —CH(CH₃)—C(=O)-LG, —CH=CH—C(=O)-LG or —N(R²⁰)—CH₂—C(=O)-LG, wherein LG denotes a leaving group, preferably a halogen atom, particularly preferably a chlorine atom and R²⁰ denotes the same as above, is reacted in a reaction medium selected from the following: dimethylformamide, xylene, mesitylene, toluene, acetonitrile, dichloromethane, diethyl ether, tetrahydrofuran and dimethyl sulphoxide, in the presence of at least one base, preferably in the presence of at least one organic base selected from the following: triethylamine, diisopropylethylamine, N-methylmorpholine, pyridine and dimethylaminopyridine, with at least one compound of the general formula H—B-D; wherein the group H—B has at least one —N(H)— group, H₂N—B-D, H₂N—F, H₂N—(CH₂)—F, H₂N—(CH₂)—(CH₂)—F or H₂N—CH(CH₃)—F; wherein B, D and F denote the same as above;

or at least one compound of the general formula II, wherein R¹ and n denote the same as above and X represents —NH₂, —(CH₂)—NH₂, —CH(CH₃)—NH₂, —(CH₂)—(CH₂)—NH₂ or —CH=CH—NH₂, is reacted in a reaction medium, preferably a reaction medium selected from the following: dimethylformamide, xylene, mesitylene, toluene, acetonitrile, dichloromethane, diethyl ether, tetrahydrofuran and dimethyl sulphoxide, in the presence of at least one base, preferably in the presence of at least one organic base selected from the following: triethylamine, diisopropylethylamine, N-methylmorpholine, pyridine and dimethylaminopyridine, with at least one compound of the general formula F—C(=O)-LG, F—(CH₂)—C(=O)-LG, F—(CH₂)—(CH₂)—C(=O)-LG, F—CH(CH₃)—C(=O)-LG, F—CH=CH—C(=O)-LG and F—N(R²⁰)—CH₂—C(=O)-LG; wherein F, R²⁰ and LG denote the same as above;

and is converted to at least one compound of the general formula I, wherein R¹ and n denote the same as above and R² represents -A-B-D or -E-F, wherein A represents —N(R⁵)—C(=O)—; E represents a group selected from the following: —CH=CH—C(=O)—N(R¹¹)—, —(CH₂)—N(R¹⁸)—C(=O)—CH(CH₃)—, —C(=O)—N(R¹⁹)—(CH₂)—, —N(R²⁰)—(CH₂)—C(=O)—N(R²¹)—, —(CH₂)—(CH₂)—N(R²²)—C(=O)— and —CH(CH₃)—N(R²³)—C(=O)—; wherein R⁵, R¹¹, R¹⁸, R¹⁹, R²⁰, R²¹, R²² and R²³ each represent a hydrogen group; and B, D and F denote the same as above; and this compound is possibly purified and/or isolated;

and possibly at least one compound of the general formula I, wherein $R^1$ and n denote the same as above and $R^2$ represents -A-B-D or -E-F, wherein A represents —N($R^5$)—C(=O)—; E represents a group selected from the following: —CH=CH—C(=O)—N($R^{11}$), —(CH$_2$)—N($R^{18}$)—C(=O)—CH(CH$_3$)—, —C(=O)—N($R^{19}$)—(CH$_2$)—, —N($R^{20}$)—(CH$_2$)—C(=O)—N($R^{21}$)—, —(CH$_2$)—(CH$_2$)—N($R^{22}$)—C(=O)— and —CH(CH$_3$)—N($R^{23}$)—C(=O)—; wherein $R^5$, $R^{11}$, $R^{18}$, $R^{19}$, $R^{20}$, $R^{21}$, $R^{22}$ and $R^{23}$ each represent a hydrogen group; and B, D and F denote the same as above; is reacted in a reaction medium, preferably in a reaction medium selected from the following: dimethylformamide, xylene, mesitylene, toluene, acetonitrile, dichloromethane, diethyl ether, tetrahydrofuran and dimethyl sulphoxide, in the presence of a base, preferably in the presence of a metal hydride salt, particularly preferably in the presence of potassium hydride and/or sodium hydride with at least one compound of the general formula LG-$R^5$, LG-$R^{11}$, LG-$R^{18}$, LG-$R^{19}$, LG-$R^{20}$, LG-$R^{21}$, LG-$R^{22}$ or LG-$R^{23}$, wherein $R^5$, $R^{11}$, $R^1$, $R^{19}$, $R^{20}$, $R^{21}$, $R^{22}$ and $R^{23}$ denote the same as above with the exception of hydrogen, and is converted to at least one compound of the general formula I, wherein $R^1$ and n denote the same as above and $R^2$ represents -A-B-D or -E-F, wherein A represents —N($R^5$)—C(=O)—; E represents a group selected from the following: —CH=CH—C(=O)—N($R^{11}$), —(CH$_2$)—N($R^{18}$)—C(=O)—CH(CH$_3$)—, —C(=O)—N($R^{19}$)—(CH$_2$)—, —N($R^{20}$)—(CH$_2$)—C(=O)—N($R^{21}$)—, —(CH$_2$)—(CH$_2$)—N($R^{22}$)—C(=O)— and —CH(CH$_3$)—N($R^{23}$)—C(=O)—; wherein $R^5$, $R^{11}$, $R^{18}$, $R^{19}$, $R^{20}$, $R^{21}$, $R^{22}$ and $R^{23}$ represent structures as per one or more of the claims 1 to 12; and B, D and F denote the same as in one or more of the claims 1 to 12; and this compound is possibly purified and/or isolated;

and possibly a compound of the general formula I, wherein $R^1$ and n denote the same as above and $R^2$ represents -A-B-D or -E-F, wherein A represents —N($R^5$)—C(=O)—; E represents a group selected from the following: —CH=CH—C(=O)—N($R^{11}$), —(CH$_2$)—N($R^{18}$)—C(=O)—CH(CH$_3$)—, —C(=O)—N($R^{19}$)—(CH$_2$)—, —N($R^{20}$)—(CH$_2$)—C(=O)—N($R^{21}$)—, —(CH$_2$)—(CH$_2$)—N($R^{22}$)—C(=O)— and —CH(CH$_3$)—N($R^{23}$)—C(=O)—; wherein $R^5$, $R^{11}$, $R^{18}$, $R^{19}$, $R^{20}$, $R^{21}$, $R^{22}$ and $R^{23}$ denote the same as above; and B, D and F denote the same as above; is reacted in a reaction medium, preferably in a reaction medium selected from the following: dimethylformamide, xylene, mesitylene, toluene, acetonitrile, dichloromethane, diethyl ether, tetrahydrofuran and dimethyl sulphoxide, with at least one compound of the general formula IV,

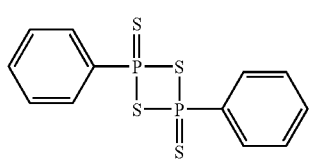

IV wherein the phenyl groups are each substituted, independently of one another, with 1 or 2 substituents selected from the following: methoxy, phenoxy, Cl, methyl and Br, preferably with a phenoxy group or a methoxy group and particularly preferably with a methoxy group in the para-position, or with phosphorus pentasulphide, and is converted to at least one compound of the general formula I, wherein $R^1$ and n denote the same as above and $R^2$ represents -A-B-D or -E-F, wherein A represents —N($R^5$)—C(=S)—; E represents a group selected from the following: —CH=CH—C(=S)—N($R^{11}$), —(CH$_2$)—N($R^{18}$)—C(=S)—CH(CH$_3$)—, —C(=S)—N($R^{19}$)—(CH$_2$)—, —N($R^{20}$)—(CH$_2$)—C(=S)—N($R^{21}$)—, —(CH$_2$)—(CH$_2$)—N($R^{22}$)—C(=S)— and —CH(CH$_3$)—N($R^{23}$)—C(=S)—; wherein $R^5$, $R^{11}$, $R^{18}$, $R^{19}$, $R^{20}$, $R^{21}$, $R^{22}$ and $R^{23}$ denote the same as above; and B, D and F denote the same as in one or more of the claims 1 to 12; and this compound is possibly purified and/or isolated.

Also the subject matter of the present invention is a method for producing compounds of the general formula I according to which at least one compound of the general formula II,

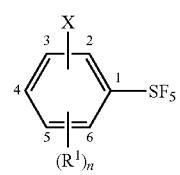

II wherein $R^1$ and n denote the same as above and X represents —NH$_2$ or —NHR$^6$; wherein $R^6$ denotes the same as above; is reacted in a reaction medium with at least one compound of the general formula A-B-D, wherein B and D denote the same as above and A represents a group selected from the following:

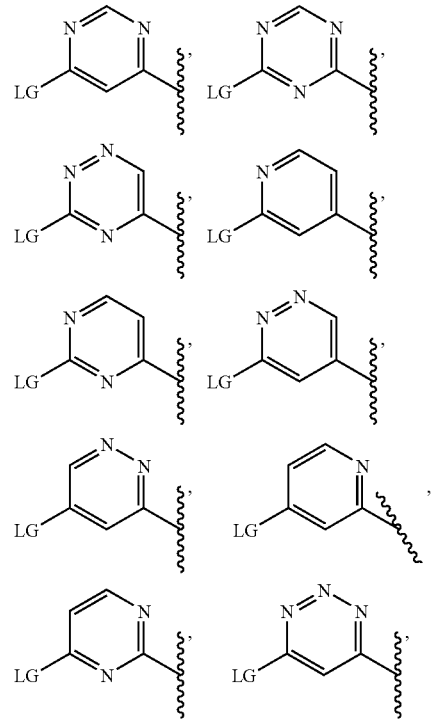

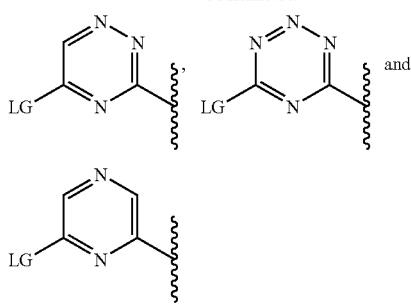

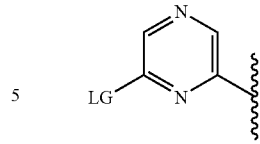

wherein LG denotes a leaving group, preferably a halogen atom, particularly preferably a fluorine atom or a chlorine atom, is reacted in a reaction medium, preferably in a reaction medium selected from the following: dimethylformamide, xylene, mesitylene, toluene, acetonitrile, dichloromethane, diethyl ether, tetrahydrofuran and dimethyl sulphoxide, and is converted to at least one compound of the general formula I, wherein $R^1$, $R^6$ and n denote the same as above and $R^2$ represents -A-B-D, wherein B and D denote the same as above and A denotes the same as above with the exception of —N($R^3$)—C(=O)—N($R^4$)—, —N($R^3$)—C(=S)—N($R^4$)—, —N($R^5$)—C(=O)— and —N($R^5$)—C(=S)—, and this compound is possibly purified and/or isolated.

The compounds with the formulae II, III, IV, A-B-D given above; wherein A represents a group selected from the following:

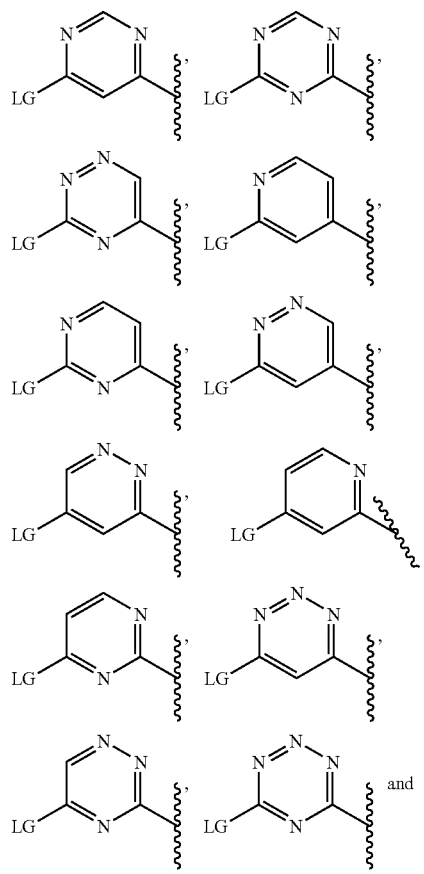

H—B-D, $H_2N$—B-D, $H_2N$—F, $H_2N$—($CH_2$)—F, $H_2N$—($CH_2$)—($CH_2$)—F, $H_2N$—CH($CH_3$)—F, F—N=C=O, F—N=C=S, F—($CH_2$)—N=C=O, F—($CH_2$)—N=C=S, F—($CH_2$)_2—($CH_2$)—N=C=O, F—($CH_2$)—($CH_2$)—N=C=S, F—CH($CH_3$)—N=C=O, F—CH($CH_3$)—N=C=S, F—C(=O)-LG, F—($CH_2$)—C(=O)-LG, F—($CH_2$)—($CH_2$)—C(=O)-LG, F—CH($CH_3$)—C(=O)-LG, F—CH=CH—C(=O)-LG, F—N($R^{20}$)—$CH_2$—C(=O)-LG, LG-$R^3$, LG-$R^4$, LG-$R^7$, LG-$R^8$, LG-$R^9$, LG-$R^{10}$, LG-$R^{12}$, LG-$R^{13}$, LG-$R^{14}$, LG-$R^{15}$, LG-$R^{16}$, LG-$R^{17}$, LG-$R^{24}$, LG-$R^{25}$, LG-G, LG-$R^5$, LG-$R^{11}$, LG-$R^{18}$, LG-$R^{19}$, LG-$R^{20}$, LG-$R^{21}$, LG-$R^{22}$ and LG-$R^{23}$ may possibly be commercially available and can also be produced using methods known to a person skilled in the art.

Production of the compounds according to the invention can also be carried out in similar manner to the methods disclosed in the following: WO 2002/8221, WO 2002/16318, WO 2002/16319, WO 2003/70247, WO 2003/80578, WO 2003/95420, WO 2004/24710, WO 2004/74290, WO 2004/89877, WO 2004/103954, WO 2004/108133, WO 2005/3084, WO 2005/7646, WO 2005/9980, WO 2005/9987, WO 2005/9977, WO 2005/16890, Park et al. Bioorg. Med. Chem. Lett. 2004, 14, 787-791, Ryu et al. Bioorg. Med. Chem. Lett. 2004, 14, 1751-1755, Park et al. Bioorg. Med. Chem. Lett. 2005, 15, 631-634 and Shao et al. Bioorg. Med. Chem. Lett. 2005, 15, 719-723. The relevant descriptions are included here by way of reference and should be considered to be part of the present disclosure.

The reactions described above can each be carried out under the usual conditions, which are familiar to a person skilled in the art, with regard to pressure or the order of addition of the compounds. Ideal process conditions may possibly be determined by a person skilled in the art by means of simple preliminary experiments. The intermediate products and end products from the reactions described above can each be purified and/or isolated using normal methods which are known to a person skilled in the art if desired and/or required. Examples of cleaning methods are extraction processes and chromatographic processes such as column chromatography or preparative chromatography. All of the aforementioned method steps and the respective purification and/or isolation of intermediate products or end products can be carried out partially or entirely under an inert atmosphere, preferably a nitrogen atmosphere.

The pentafluorosulphanyl-substituted compounds according to the invention of the above general formula I and corresponding stereoisomers thereof can be isolated in the form of their free bases, their free acids, or in the form of corresponding salts, particularly physiologically tolerable salts. The free bases of the respective pentafluorosulphanyl-substituted compounds according to the invention of the above formula and their corresponding stereoisomers can be converted, for example by reaction with an inorganic or organic acid, preferably hydrochloric acid, hydrobromic acid, sulphuric acid, phosphoric acid, methanesulphonic acid, p-toluenesulphonic acid, carbonic acid, formic acid, acetic acid, oxalic acid, succinic acid, tartaric acid, mandelic acid, fumaric acid, lactic acid, citric acid, glutamic acid or aspartic acid, into the corresponding salts, preferably physiologically tolerable salts. The free bases of the respective pentafluorosulphanyl-substituted compounds of the above formula I and their corresponding stereoisomers can also be converted with the free acid or a salt of a sugar substitute, such as saccharine, cyclamate or acesulfame.

Similarly, the free acids of the pentafluorosulphanyl-substituted compounds of the above formula I and their corresponding stereoisomers can be converted by reaction with a suitable base into the corresponding physiologically tolerable salts. Examples are alkali metal salts, alkaline earth metal salts or ammonium salts $[NH_xR_{4-x}]^+$, wherein x=0, 1, 2, 3 or 4 and R denotes a linear or branched $C_{1-4}$ alkyl group.

The pentafluorosulphanyl-substituted compounds according to the invention having the above formula I and their corresponding stereoisomers, or alternatively their corresponding acids, bases or salts, or their solvates, preferably in the form of their hydrates, may be obtained using the usual methods that are known to persons skilled in the art.

If the pentafluorosulphanyl-substituted compounds according to the invention having the above general formula I are obtained, following their production, in the form of a mixture of stereoisomers, preferably in the form of their racemates or other mixtures of their various enantiomers and/or diastereoisomers, they can be separated and possibly isolated using methods that are known to a person skilled in the art. Examples are chromatographic separation processes and particularly liquid chromatography methods under normal pressure or under raised pressure, preferably MPLC and HPLC processes, and methods for fractional crystallisation. Hereby, in particular, individual enantiomers can be separated from one another using, for example, HPLC with a chiral stationary phase or, by means of crystallisation with chiral acids, such as (+)-tartaric acid, (−)-tartaric acid or (+)-10-camphorsulphonic acid, diastereoisomeric salts can be separated from one another.

The pentafluorosulphanyl-substituted compounds according to the invention having the above general formula I and their corresponding stereoisomers, as well as their corresponding acids, bases, salts and solvates are toxicologically safe and are therefore suitable as pharmaceutically active ingredients in medicaments.

Also the subject matter of the present invention is therefore a medicament containing at least one pentafluorosulphanyl-substituted compound having the above general formula I, possibly in the form of one of its pure stereoisomers, particularly enantiomers or diastereoisomers, its racemates, or in the form of a mixture of stereoisomers, particularly the enantiomers and/or diastereoisomers, in any mixing ratio, or in the form of a corresponding salt or in the form of a corresponding solvate and possibly one or more pharmaceutically tolerable inactive ingredient.

The medicaments according to the invention are suitable in particular for vanilloid-receptor 1 (VR1/TRPV1) regulation, in particular for vanilloid receptor 1 (VR1/TRPV1) blocking or for vanilloid receptor 1 (VR1/TRPV1) stimulation.

Also preferably, the medicaments according to the invention are suitable for the prophylaxis and/or treatment of disturbances or illnesses which are at least partially mediated by vanilloid receptors 1.

Preferably, the medicament according to the invention is suitable for the treatment and/or prophylaxis of one or more conditions belonging to the following: pain, preferably pain belonging to the following: acute pain, chronic pain, neuropathic pain and visceral pain; joint pain; migraine; depression; neuropathy; neural injury; neurodegenerative conditions, preferably belonging to the following: multiple sclerosis, Alzheimer's disease, Parkinson's disease and Huntington's chorea; cognitive dysfunctions, preferably cognitive inadequacies, particularly preferably memory deficiencies; epilepsy; airway diseases, preferably belonging to the following: asthma and pulmonary inflammation; coughing; urinary incontinence; overactive bladder; gastric ulcers; irritable bowel syndrome; strokes; irritation of the eye; skin irritation; neurotic skin diseases; inflammatory conditions, preferably inflammation of the gut; diarrhoea; pruritus; eating disorders, preferably belonging to the following: bulimia, cachexia, anorexia and obesity; medicament dependency; medicament abuse; withdrawal symptoms from medicament dependency; development of tolerance to medicaments, preferably to natural or synthetic opioids; drug dependency; drug misuse; withdrawal symptoms from drug dependency; alcohol dependency; alcohol misuse and withdrawal symptoms from alcohol dependency; for diuresis; for antinatriuresis; for influencing the cardiovascular system; for increasing alertness; for increasing libido; for modulating motor activity; for anxiolysis; for local anaesthesia and/or inhibiting unwanted side-effects, preferably belonging to the following: hyperthermia, raised blood pressure and narrowing of the bronchi, triggered by administration of vanilloid receptor 1 (VR1/TRPV1-receptor) agonists, preferably belonging to the following: capsaicin, resiniferatoxin, olvanil, arvanil, SDZ-249665, SDZ-249482, nuvanil and capsavanil.

Particularly preferably, the medicament according to the invention is suitable for the treatment and/or prophylaxis of one or more conditions belonging to the following: pain, preferably pain belonging to the following: acute pain, chronic pain, neuropathic pain and visceral pain; migraine; depression; neurodegenerative conditions, preferably belonging to the following: multiple sclerosis, Alzheimer's disease, Parkinson's disease and Huntington's chorea; cognitive dysfunctions, preferably cognitive inadequacies, particularly preferably memory deficiencies; urinary incontinence; overactive bladder; medicament dependency; medicament misuse; withdrawal symptoms from medicament dependency; development of tolerance to medicaments, preferably development of tolerance to natural or synthetic opioids; drug dependency; drug misuse; withdrawal symptoms from drug dependency; alcohol dependency; alcohol misuse and withdrawal symptoms from alcohol dependency.

Especially preferably, the medicament according to the invention is suitable for the treatment and/or prophylaxis of pain, preferably pain belonging to the following: acute pain, chronic pain, neuropathic pain or visceral pain, and/or urinary incontinence.

Also the subject matter of the present invention is the use of at least one pentafluorosulphanyl-substituted compound according to the invention and possibly one or more pharmaceutically tolerable inactive ingredients for producing a medicament for vanilloid receptor 1 (VR1/TRPV1)-regulation, preferably for vanilloid receptor 1 (VR1/TRPV1)-blocking and/or for vanilloid receptor 1 (VR1/TRPV1)-stimulation.

Preferable is the use of at least one pentafluorosulphanyl-substituted compound according to the invention and possibly one or more pharmaceutically tolerable inactive ingredients for producing a medicament for the prophylaxis and/or treatment of disorders or diseases which are at least partially mediated by vanilloid receptors 1.

Particularly preferable is the use of at least one pentafluorosulphanyl-substituted compound according to the invention and possibly one or more pharmaceutically tolerable inactive ingredients for producing a medicament for the treatment and/or prophylaxis of one or more conditions belonging to the following: pain, preferably pain belonging to the following: acute pain, chronic pain, neuropathic pain and visceral pain; joint pain; migraine; depression; neuropathy; neural injury; neurodegenerative conditions, preferably belonging to the following: multiple sclerosis, Alzheimer's disease, Parkinson's disease and Huntington's chorea; cognitive dysfunctions, preferably cognitive inadequacies, particularly preferably memory deficiencies; epilepsy; airway diseases, preferably belonging to the following: asthma and pulmonary inflammation; coughing; urinary incontinence; overactive bladder; gastric ulcers; irritable bowel syndrome; strokes; irritation of the eye; skin irritation; neurotic skin diseases; inflammatory conditions, preferably inflammation of the gut; diarrhoea; pruritus; eating disorders, preferably belonging to the following: bulimia, cachexia, anorexia and obesity; medicament dependency; medicament abuse; withdrawal symptoms from medicament dependency; development of tolerance to medicaments, preferably to natural or synthetic opioids; drug dependency; drug misuse; withdrawal symptoms from drug dependency; alcohol dependency; alcohol misuse and withdrawal symptoms from alcohol dependency; for diuresis; for antinatriuresis; for influencing the cardiovascular system; for increasing alertness; for increasing libido; for modulating motor activity; for anxiolysis; for local anaesthesia and/or inhibiting unwanted side-effects, preferably belonging to the following: hyperthermia, raised blood pressure and narrowing of the bronchi, triggered by administration of vanilloid receptor 1 (VR1/TRPV1-receptor) agonists, preferably belonging to the following: capsaicin, resiniferatoxin, olvanil, arvanil, SDZ-249665, SDZ-249482, nuvanil and capsavanil.

Especially preferable is the use of at least one pentafluorosulphanyl-substituted compound according to the invention and possibly one or more pharmaceutically tolerable inactive ingredients for producing a medicament for the treatment and/or prophylaxis of prophylaxis of one or more conditions belonging to the following: pain, preferably pain belonging to the following: acute pain, chronic pain, neuropathic pain and visceral pain; migraine; depression; neurodegenerative conditions, preferably belonging to the following: multiple sclerosis, Alzheimer's disease, Parkinson's disease and Huntington's chorea; cognitive dysfunctions, preferably cognitive inadequacies, particularly preferably memory deficiencies; urinary incontinence; overactive bladder; medicament dependency; medicament abuse; withdrawal symptoms from medicament dependency; development of tolerance to medicaments, preferably development of tolerance to natural or synthetic opioids; drug dependency; drug misuse; withdrawal symptoms from drug dependency; alcohol dependency; alcohol misuse and withdrawal symptoms from alcohol dependency.

Still more preferable is the use of at least one pentafluorosulphanyl-substituted compound according to the invention and possibly one or more pharmaceutically tolerable inactive ingredients for producing a medicament for treatment and/or prophylaxis of pain, preferably pain belonging to the following: acute pain, chronic pain, neuropathic pain or visceral pain, and/or urinary incontinence.

The medicament according to the invention is suitable for administration to adults and children including infants and breast-feeding babies. The medicament according to the invention may exist in a liquid, semisolid or solid pharmaceutical form, for example in the form of injection solutions, drops, juices, syrups, sprays, suspensions, tablets, patches, capsules, plasters, suppositories, ointments, creams, lotions, gels, emulsions, aerosols or in multiparticulate form, for example, in the form of pellets or granulates, possibly pressed into tablets, placed in capsules or suspended in a liquid, and may also be administered as such.

Alongside at least one pentafluorosulphanyl-substituted compound of the above general formula I, possibly in the form of its pure stereoisomers, in particular enantiomers or diastereoisomers, its racemates or in the form of mixtures of the stereoisomers, in particular the enantiomers or diastereoisomers, in any desired mixing ratio or possibly in the form of a corresponding salt or in the form of a corresponding solvate, the medicament according to the invention usually contains further physiologically tolerable pharmaceutically inactive ingredients, which are selected, for example, from the following: support materials, fillers, solvents, diluting agents, surfactants, colouring agents, preservatives, disintegrants, lubricants, glidants, flavourings and binding agents.

The choice of physiologically tolerable inactive ingredients and the quantities thereof that are used depends on whether administration of the medicament is to be oral, subcutaneous, parenteral, intravenous, intraperitoneal, intradermal, intramuscular, intranasal, buccal, rectal or topical (for example, on infections of the skin, the mucous membranes or on the eyes). For oral application, preparations in the form of tablets, sugar-coated tablets, capsules, granulates, pellets, drops, juices and syrups are suitable, whilst for parenteral, topical and inhalation application, solutions, suspensions, readily reconstituted dry preparations and sprays are suitable. The pentafluorosulphanyl-substituted compounds used in the medicaments according to the invention may be in a depot, in dissolved form or in a plaster, possibly with the addition of agents to promote penetration of the skin are suitable percutaneous application preparations. Orally or percutaneously applicable preparation forms may also delay the release of the respective pentafluorosulphanyl-substituted compounds according to the invention.

Production of the medicament according to the invention is carried out with the aid of the usual prior art equipment, devices, methods and procedures as described, for example, in "Remington's Pharmaceutical Sciences", edited by A. R. Gennaro, 17$^{th}$ edition, Mack Publishing Company, Easton, Pa., USA, 1985, and particularly as described in Part 8, chapters 76 to 93. The relevant description is included here as a reference and is intended as part of the disclosure. The quantity of the relevant pentafluorosulphanyl-substituted compound of the above general formula I to be administered to the patient may vary and is dependent, for example, on the weight or age of the patient and the method of application, the indication and the severity of the condition. Usually in the range of 0.001 mg/kg to 100 mg/kg, preferably in the range of 0.05 mg/kg to 75 mg/kg, particularly preferably in the range of 0.05 mg/kg to 50 mg/kg body weight of the patient of such a compound according to the invention is applied.

Pharmacological Methods:

I. Functional Investigation Using the Vanilloid Receptor 1 (VR1/TRPV1 Receptor)

The agonistic and antagonistic effects of the substances under investigation on the vanilloid receptor 1 (VR1/TRPV1) of the rat can be determined using the following assay. According to this assay, the $Ca^{2+}$ influx through the receptor channel is quantified with the aid of a $Ca^{2+}$-sensitive dye (of the type Fluo-4, from Molecular Probes Europe BV, Leiden, Netherlands) in a Fluorescent Imaging Plate Reader (FLIPR, from Molecular Devices, Sunnyvale, USA).

Methods:

Complete medium: 10% by volume FCS (foetal calf serum, from Gibco Invitrogen GmbH, Karlsruhe, Germany, heat deactivated);

2 mM L-glutamine (from Sigma, Munich, Germany);

1% by weight of AA solution (antibiotic/antimycotic solution, from PAA, Pasching, Austria) and 25 ng/ml Medium NGF (2.5 S, from Gibco Invitrogen GmbH, Karlsruhe, Germany)

Cell culture plate: poly-D-lysine-coated, black 96-well plates with clear bases (96 well black/clear plate, from BD Biosciences, Heidelberg, Germany) were also coated with laminin (from Gibco Invitrogen GmbH, Karlsruhe, Germany), in that the laminin was diluted to a concentration of 100 μg/ml with PBS (Ca—Mg-free PBS, from Gibco Invitrogen GmbH, Karlsruhe, Germany). Aliquots with a concentration of 100 μg/ml of laminin were taken and stored at −20° C. The aliquots were diluted with PBS in a ratio of 1:10 to 10 μg/ml laminin and 50 μl of the solution was pipetted into each well in the cell culture plate. The cell culture plates were then incubated for at least two hours at 37° C., the residual solution drawn off and the wells washed twice with PBS. The coated cell culture plates were stored with the residual PBS, which was removed immediately before offering up the cells.

Preparation of the Cells:

The spinal column was removed from decapitated rats and laid directly into cold (placed in an ice bath) HBSS buffer (Hank's buffered saline solution, from Gibco Invitrogen GmbH, Karlsruhe, Germany) to which was added 1% by volume of an AA-solution (antibiotic/antimycotic solution, from PAA, Pasching, Austria). The spinal column was bisected longitudinally and removed, together with the fasciae, from the vertebral canal. The dorsal root ganglia (DRGs) were then removed and again placed in cold HBSS buffer to which was added 1% by volume of an AA-solution, and stored. The DRGs, completely freed from residual blood and spinal nerves were transferred, in each case, into 500 μl cold collagenase type 2 (from PAA, Pasching, Austria) and incubated for 35 minutes at 37° C. Following addition of 2.5% by volume of trypsin (from PAA, Pasching, Austria), the material was incubated for a further 10 minutes at 37° C. Following complete incubation, the enzyme solution was carefully pipetted off and 500 μl complete medium was added to the remaining DRGs. The DRGs were suspended several times in each case, drawn by means of a syringe through No. 1, No. 12 and No. 16 cannulae and transferred to 50 ml Falcon tubes and these then filled to 15 ml with complete medium. The contents of each Falcon tube was filtered through a 70 μm Falcon filter insert and centrifuged for 10 minutes at 1200 revolutions and at room temperature. The resulting pellet was added, in each case, to 250 μl complete medium and the cell count was determined.

The number of cells in the suspension was adjusted to $3 \times 10^5$ per ml and, in each case, 150 μl of this suspension was placed in a well in the coated cell culture plate of the type described above. The plates were left in an incubation cupboard at 37° C. under 5% by volume $CO_2$ and 95% relative humidity for two to three days.

Subsequently, the cells were placed, together with 2 μM Fluo-4 and 0.01% by volume Pluronic F127 (from Molecular Probes Europe BV, Leiden, Netherlands), into HBSS buffer (Hank's buffered saline solution, from Gibco Invitrogen GmbH, Karlsruhe, Germany) for 30 minutes at 37° C., washed 3 times with HBSS buffer and, following a further incubation period of 15 minutes at room temperature, placed in the FLIPR assay for $Ca^{2+}$ measurement. The $Ca^{2+}$-dependent fluorescence was measured before and after addition of substances ($\lambda_{ex}$=488 nm, $\lambda_{em}$=540 nm). Quantification took place by measuring the highest intensity of fluorescence (FC, fluorescence counts) over time.

FLIPR Assay:

The FLIPR protocol comprises 2 substance additions. Initially, the compounds to be tested (1 μM) were pipetted onto the cells and the $Ca^{2+}$ influx compared with the control (capsaicin 1 μM). This results in the % value for activation related to the $Ca^{2+}$ signal following addition of 1 μM capsaicin (CP). Following 5 minutes of incubation, 100 nM capsaicin were applied and the influx of $Ca^{2+}$ determined again. Desensitising agonists and antagonists lead to a suppression of the $Ca^{2+}$ influx. % inhibition is calculated, compared with the maximum achievable inhibition with 10 μM capsaicin.

Triple determination was carried out (n=3) and this was repeated in at least 3 independent experiments (N=4).

II. Functional Investigation Using the Vanilloid Receptor (VR1)

The agonistic or antagonistic effect of the substances to be investigated on the vanilloid receptor (VR1) can also be determined with the following assay. According to this assay, the $Ca^{2+}$ influx through the channel can be quantified with the aid of a $Ca^{2+}$ sensitive dye (of the type Fluo-4, from Molecular Probes, Europe BV, Leiden, Netherlands) in a Fluorescent Imaging Plate Reader (FLIPR, from Molecular Devices, Sunnyvale, USA).

Method:

Chinese hamster ovary cells (CHO K1-cells, from the European Collection of Cell Cultures (ECACC), UK) were stably transfected with the VR1 gene. For functional investigations, these cells were plated out on Poly-D-lysine-coated, black 96-well plates with clear bases (from BD Biosciences, Heidelberg, Germany) at a density of 25,000 cells/well. The cells were incubated over night at 37° C. and under 5% $CO_2$ in a culture medium (Nutrient Mixture Ham's F12, 10% by volume FCS (foetal calf serum), 18 μg/ml L-proline). The following day, the cells were incubated with Fluo-4 (Fluo-4 2 μM, Pluronic F127 0.01% by volume, from Molecular Probes in HBSS (Hank's buffered saline solution), from Gibco Invitrogen GmbH, Karlsruhe, Germany) for 30 minutes at 37° C. Subsequently, the plates were washed 3 times with HBSS buffer and, following a further period of incubation for 15 minutes at room temperature, placed in the FLIPR for $Ca^{2+}$ measurement. The $Ca^{2+}$-dependent fluorescence was measured before and after the addition of the substances to be investigated (wavelength $\lambda_{BX}$=488 nm, $\lambda_{em}$=540 nm). Quantification took place by measuring the highest intensity of fluorescence (FC, fluorescence counts) over time.

FLIPR Assay:

The FLIPR protocol comprises 2 substance additions. Initially, the substances to be tested (10 μM) were pipetted onto the cells and the $Ca^{2+}$ influx was compared with the control (capsaicin 10 μM) (% activation related to the $Ca^{2+}$ signal following addition of 10 μM capsaicin). Following 5 minutes of incubation, 100 nM capsaicin were applied and the $Ca^{2+}$ influx determined again.

Desensitising agonists and antagonists lead to a suppression of the $Ca^{2+}$ influx. % inhibition is calculated, compared with the maximum achievable inhibition with 10 μM capsaicin.

II. Formalin Test in Mouse

Investigation to determine the antinociceptive effects of the compounds according to the invention was carried out using the formalin test on male mice (NMRI, 20 to 30 g body weight, from Iffa, Credo, Belgium).

Using the formalin test, as per D. Dubuisson et al., Pain 1977, 4, 161-174, the first (early) phase (0 to 15 minutes after the formalin injection) and the second (late) phase (15 to 60 minutes after the formalin injection) are distinguished. The early phase represents a model for acute pain, as the direct reaction to the formalin injection, whereas the late phase is regarded as a model for persistent (chronic) pain (T. J. Coderre et al., Pain 1993, 52, 259-285). The relevant descriptions in the literature are included here as a reference and are intended as part of the disclosure.

The compounds according to the invention were investigated in the second phase of the formalin test in order to obtain information about the effects of the substances on chronic/inflammatory pain.

The time point of the application of the compounds according to the invention before the formalin injection was chosen depending on the mode of application of the compounds according to the invention. Intravenous application of 10 mg/kg body weight of test substances was carried out 5 minutes before the formalin injection. The latter was then applied with a single subcutaneous injection (20 μl, 1% aqueous solution) into the dorsal side of the right rear foot, so that in freely mobile test animals, a nociceptive reaction was induced, which expressed itself as marked licking and biting of the affected foot.

Subsequently, in the second (late) phase of the formalin test (21 to 24 minutes after the formalin injection), the nociceptive behaviour was recorded by observing the animals continuously. Quantification of the pain response was made by totalling the number of seconds during which the animals showed licking and biting of the affected foot during the observation period.

The comparison was made in each case with control animals which, in place of the compounds according to the invention, were given vehicle material (0.9% aqueous sodium chloride solution) before the formalin application. Based on the quantification of the pain response, the effect of the substance in the formalin test was determined as a percentage change, relative to the respective control.

After injection of substances that have an antinociceptive effect in the formalin test, the described behaviours of the animals, that is licking and biting, were found to be reduced or absent.

IV. Investigation of Analgesic Effect Using the Writhing Test

Investigation of the compounds according to the invention of the general formula I for analgesic efficacy was performed using phenylquinone-induced writhing in the mouse, modified as described by I. C. Hendershot and J. Forsaith (1959) J. Pharmacol. Exp. Ther. 125, 237-240. The relevant literature citation is included here as a reference and is intended as part of the disclosure.

Male NMRI mice with a weight in the range of 25 g to 30 g were used. 10 minutes after intravenous administration of the compounds to be investigated, groups of 10 animals per compound dose were given intraperitoneal applications of 0.3 ml/mouse of a 0.02% aqueous solution of phenylquinone (phenylbenzoquinone, from Sigma, Deisenhofen, Germany; solution made with the addition of 5% by weight of ethanol and then placement in a water bath at 45° C.). The animals were placed individually in observation cages. Using a push-button counter, the number of pain-induced stretching movements (writhing reactions=straightening of the body with stretching of the rear extremities) was counted 5 to 20 minutes following the phenylquinone administration. By way of a control, animals were included which had received only physiological saline solution. All the compounds were tested at the standard dosage of 10 mg/kg.

The invention will now be described by way of illustrations. These illustrations are purely exemplary and do not restrict the general concept of the invention.

EXAMPLES

The yields of the compounds produced have not been optimised.

All temperature values are uncorrected.

The chemicals and solvents used were commercially obtained from the usual suppliers (Acros, Avocado, Aldrich, Bachem, Fluka, Lancaster, Maybridge, Merck, Sigma, Solvias (Base, Switzerland for $SF_5$-containing reagents) AG, TCI, etc.) or synthesised in accordance with methods known to persons skilled in the art.

As the stationary phase for the column chromatography, silica gel 60 (0.040 mm-0.063 mm) from E. Merck, Darmstadt, Germany was used.

Thin layer chromatographic investigations were carried out with HPTLC plates and silica gel 60 F 254, from E. Merck, Darmstadt, Germany.

The mixing ratios of solvents or liquid phases for chromatographic investigations are always given in volume/volume.

Analysis was carried out using mass spectroscopy and NMR.

Synthesis of Example Compound 1:

N-{4-[3-(4-pentafluorosulphanyl-benzyl)-thioureidomethyl]-2-fluoro-phenyl}-methane sulphonamide

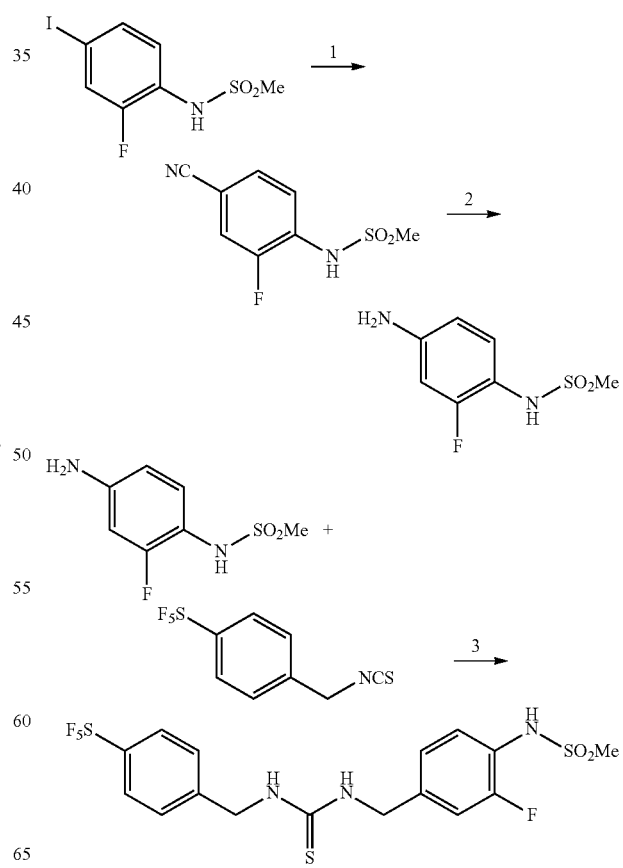

1. Synthesis of N-(4-cyano-2-fluoro-phenyl)-methane sulphonamide

A suspension of N-(2-fluoro-4-iodo-phenyl)-methane sulphonamide (2.57 g, 8.15 mmol), zinc(II)cyanide (570 mg, 4.89 mmol) and tetrakis(triphenylphosphine)palladium (470 mg, 0.41 mmol) in dimethylformamide (15 ml) was stirred for 8 h at 80° C. and for 40 h at room temperature.

Water (15 ml) was added to the reaction mixture, the precipitate formed was drawn off and the filtrate was extracted several times with ethyl acetate. The combined organic phases were washed with water, dried and the solvent removed under vacuum. Dimethylformamide residues were removed by codistillation with toluene. The residue was left to stand for crystallisation. The desired product was obtained as a white solid (1.15 g).

2. Synthesis von N-(4-aminomethyl-2-fluoro-phenyl)-methane sulphonamide

The catalyst (0.151 g Raney nickel), N-(4-cyano-2-fluoro-phenyl)-methane sulphonamide (1.15 g) and methanol (25 ml) were placed in a hydrogenator. The mixture was stirred over night under hydrogen at a pressure of 2 bar. 0.26 ml hydrogen was taken up. The reaction mixture was drawn off through the filtering material and the filter cake was washed with methanol. The solvent was removed under vacuum and the residue was dried. The desired product was obtained in the form of a solid (476 mg).

3. Synthesis of N-{4-[3-(4-pentafluorosulphanyl-benzyl)-thioureidomethyl]-2-fluoro-phenyl}-methane sulphonamide N-(4-aminomethyl-2-fluoro-phenyl)-methane sulphonamide (237 mg, 1.09 mmol) was dissolved in dimethylformamide (1 ml) and to this was added triethylamine (132 mg, 1.30 mmol) and 4-(pentafluorosulphanyl)benzylisothiocyanate (300 mg, 1.09 mmol) dissolved in dimethylformamide (1 ml). The reaction mixture was stirred over night at room temperature, the solvent removed under vacuum and the residue dissolved in a little methanol. Following column chromatographic cleaning (silica gel, hexane/ethyl acetate 1:5), the product was obtained as a solid (305 mg, 57% of the theoretical amount).

Synthesis of Example Compound 2:

4-(3-chloro-pyridin-2-yl)-piperazine-1-carboxy-(4-pentafluorosulphanyl-phenyl)-amide

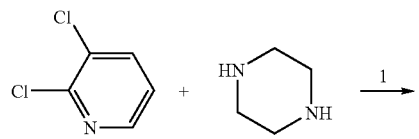

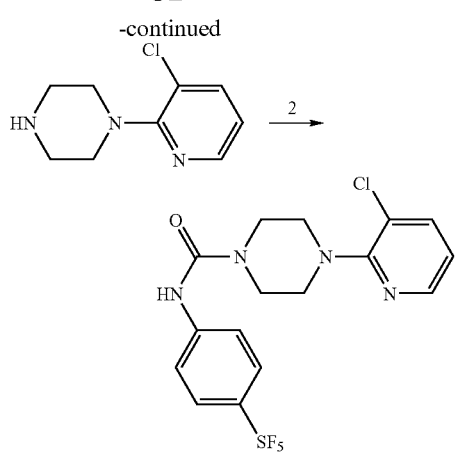

1. Synthesis of 1-(3-chloro-pyridin-2-yl)-piperazine

Piperazine (15 g, 174 mmol) was dissolved in dimethyl sulphoxide (309 g) and to this was added 2,3-dichloropyridine (23.4 g, 158 mmol). The reaction mixture was stirred for 60 h at 110° C. Portions of saturated aqueous sodium hydrogencarbonate solution (overall 250 ml) were added to the reaction mixture and the precipitate produced was drawn off. The filtrate was extracted several times with ethyl acetate (150 ml each time) and the cleaned organic phase was dried and the solvent was removed under vacuum. The residue was distilled at $2 \times 10^{-1}$ mbar. The product was obtained at an overhead temperature of 95° C. and a bottom temperature of 155° C. Yield: 9.6 g (28% of the theoretical amount).

2. Synthesis of 4-(3-chloro-pyridin-2-yl)-piperazine-1-carboxy-(4-pentafluorosulphanyl-phenyl)-amide 1-(3-chloro-pyridin-2-yl)-piperazine (403 mg, 2.04 mmol) was dissolved in dimethylformamide (1 ml) and to this was added triethylamine (247 mg, 2.48 mmol) and 4-(pentafluorosulphanyl)-phenylisocyanate (500 mg, 2.039 mmol) dissolved in dimethylformamide (1 ml). The reaction mixture was stirred over night at room temperature, the solvent was removed under vacuum and the residue was dissolved in methanol. Following column chromatographic purification (silica gel, hexane/ethyl acetate 1:1), the product was obtained as a solid (684 mg, 75% of the theoretical amount).

Synthesis of Example Compound 3:

4-(3-chloro-pyridin-2-yl)-piperazine-1-thiocarboxy-(4-pentafluorosulphanyl-phenyl)-amide 1-(3-chloro-pyridin-2-yl)-piperazine (226 mg, 1.14 mmol) was dissolved in dimethylformamide (1 ml) and to this was added triethylamine (140 mg, 1.38 mmol) and 4-(pentafluorosulphanyl)-phenylisothiocyanate (300 mg, 1.14 mmol) dissolved in dimethylformamide (1 ml). The reaction mixture was stirred over night at room temperature, the solvent removed under vacuum and the residue was dissolved in a little methanol. Following column chromatographic cleaning (silica gel, hexane/ethyl acetate 1:1), the product was obtained as a solid (315 mg, 60% of the theoretical amount).

The example compounds 9, 10, 18, 19, 20, 21 and 22 below were made in similar manner to the example compounds 1 to 3. The required starting compounds are known to persons skilled in the art.

1. N-{4-[3-(4-pentafluorosulphanyl-benzyl)-thioureidomethyl]-2-fluoro-phenyl}-methanesulphonamide
2. 4-(3-chloro-pyridin-2-yl)-piperazine-1-carboxy-(4-pentafluorosulphanyl-phenyl)-amide
3. 4-(3-chloro-pyridin-2-yl)-piperazine-1-thiocarboxy-(4-pentafluorosulphanyl-phenyl)-amide
4. 3-(4-pentafluorosulphanyl-phenyl)-N-(2,3-dihydro-benzo[1,4]dioxin-6-yl)-acrylamide
5. N-(4-pentafluorosulphanyl-benzyl)-2-(3-fluoro-4-methanesulphonylamino-phenyl)-propionamide
6. (2R)-N-(4-pentafluorosulphanyl-benzyl)-2-(3-fluoro-4-methanesulphonylamino-phenyl)-propionamide
7. (2S)-N-(4-pentafluorosulphanyl-benzyl)-2-(3-fluoro-4-methanesulphonylamino-phenyl)-propionamide
8. N-(4-pentafluorosulphanyl-phenyl)-4-pyridin-2-yl-benzamide
9. 1-(4-pentafluorosulphanyl-benzyl)-3-(7-hydroxy-naphthalen-1-yl)-urea
10. 4-(3-chloro-pyrazin-2-yl)-3,6-dihydro-2H-pyridin-1-carboxy-(4-pentafluorosulphanyl-phenyl)-amide
11. (4-pentafluorosulphanyl-phenyl)-[4-(4-methyl-piperazin-1-yl)-6-(2-trifluoromethyl-benzyloxy)-[1,3,5]triazin-2-yl]-amine
12. (4-pentafluorosulphanyll-phenyl)-[6-(4-chloro-phenyl)-pyrimidin-4-yl]-amine
13. 4-pentafluorosulphanyl-N-(2-oxo-2,3-dihydro-1H-benzoimidazol-5-ylmethyl)-benzamide
14. (4-pentafluorosulphanyl-phenyl)-{6-[4-(3-chloro-pyridin-2-yl)-2-(R)-methyl-piperazin-1-yl]-pyrimidin-4-yl}-amine
15. 3'-chloro-3,6-dihydro-2H-[1,2']bipyridinyl-4-carboxy-(4-pentafluorosulphanyl-phenyl)-amide
16. 2-(4-pentafluorosulphanyl-phenylamino)-N-(7-hydroxy-naphthalen-1-yl)-acetamide
17. (4-pentafluorosulphanyl-phenyl)-[7-(3-trifluoromethyl-pyridin-2-yl)-[1,2,4]triazolo[4,3-b]pyridazin-3-yl]-amine
18. 1-(4-pentafluorosulphanyl-benzyl)-3-isoquinolin-5-yl-urea
19. 1-[2-(4-pentafluorosulphanyl-phenyl)-ethyl]-3-isoquinolin-5-yl-urea
20. 1-(4-pentafluorosulphanyl-phenyl)-3-(7-hydroxy-5,6,7,8-tetrahydro-naphthalen-1-yl)-urea
21. 1-[2-(4-pentafluorosulphanyl-phenyl)-ethyl]-3-quinolin-5-yl-urea
22. 1-(4-pentafluorosulphanyl-phenyl)-3-(1-isoquinolin-5-yl-pyrrolidin-3-yl)-urea
23. 5-pentafluorosulphanyl-2-[4-(3-chloro-pyridin-2-yl)-piperazin-1-yl]-benzooxazole
24. N-{4-[3-(4-pentafluorosulphanyl-benzyl)-ureidomethyl]-2-fluoro-phenyl}-methanesulphonamide Pharmacological Data The affinity of the pentafluorosulphanyl-substituted compounds according to the invention for the vanilloid receptor 1 (VR1/TRPV1 receptor) was determined as described above.

| Compound as per example number | VR1 (rat) (% stimulation compared with 1 μM CP) | VR1 (rat) (% blocking compared with 1 μM CP) | VR1 (human) (% stimulation compared with 1 μM CP) | VR1 (human) (% blocking compared with 1 μM CP) |
|---|---|---|---|---|
| 1 | 0.02 | 90.27 | 0.68 | 87.67 |
| 2 | 0.63 | 101.93 | 3.72 | 105.44 |

| Compound as per example number | IC$_{50}$ (rat) (μM) | IC$_{50}$ (human) (μM) | Binding K$_i$ (μM) |
|---|---|---|---|
| 1 | 0.36 | 0.8 | 0.084 |
| 2 | 0.048 | 0.25 | 0.012 |
| 3 | | | 0.094 |

The invention claimed is:

1. A pentafluorosulphanyl-substituted compound corresponding to formula I

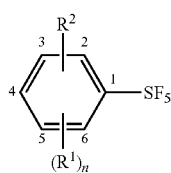

wherein
n is 0, 1, 2, 3 or 4;
R$^1$ represents one or more mutually independent groups selected from the group consisting of H, F, Cl, Br, I, —CN, —NC, —NO$_2$, —SO$_3$H, —S(=O$_2$)NH$_2$, —NH$_2$, —OH, —SH, methyl, ethyl, n-propyl, isopropyl, n-butyl, sec-butyl, isobutyl, tert-butyl, n-pentyl, sec-pentyl, n-hexyl, —O—CH$_3$, —O—C$_2$H$_5$, —O—CH(CH$_3$)$_2$, —O—C(CH$_3$)$_3$, —S—CH$_3$, —S—C$_2$H$_5$, —S—CH(CH$_3$)$_2$, —S—C(CH$_3$)$_3$, —N(CH$_3$)$_2$, —N(C$_2$H$_5$)$_2$, —NH—CH$_3$, —NH—C$_2$H$_5$, —NH—C(=O)—CH$_3$, —NH—C(=O)—C$_2$H$_5$, —C(=O)—NH$_2$, —C(=O)—CH$_3$, —C(=O)—C$_2$H$_5$, —C(=O)—OH, —C(=O)—OCH$_3$ and —C(=O)—OC$_2$H$_5$;

R$^2$ represents
  a group -A-B-D, -E-F or —N(H)-G, which can be bound to position 2, 3, 4, 5 or 6 of the phenyl group of formula I; or
  a group -Q-B-D; wherein Q represents a group selected from the group consisting of: oxazolyl, thiazolyl, isoxazolyl, isothiazolyl and imidazolyl, which is condensed with the phenyl group of formula I and thereby forms a optionally substituted group selected from the group consisting of:
  benzoxazolyl, benzothiazolyl, benzisothiazolyl and benzimidazolyl;

A represents a group selected from the group consisting of:
—N(R$^3$)—C(=O)—N(R$^4$)—, —N(R$^3$)—C(=S)—N(R$^4$)—, —N(R$^5$)—C(=O)—, —N(R$^5$)—C(=S)—,

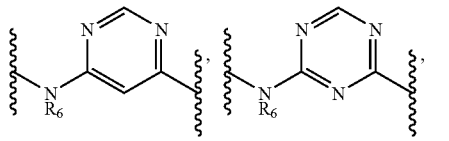,

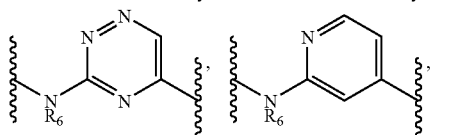,

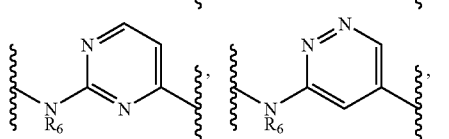,

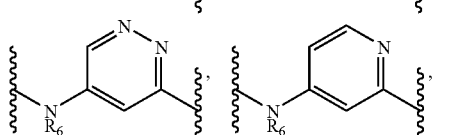,

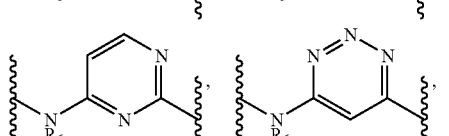,

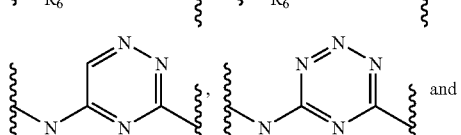,

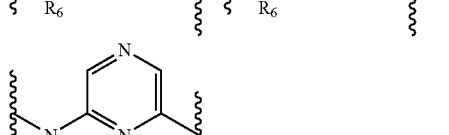 and

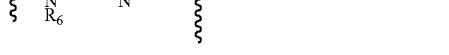

B represents a group selected from the group consisting of:

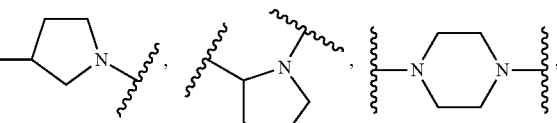

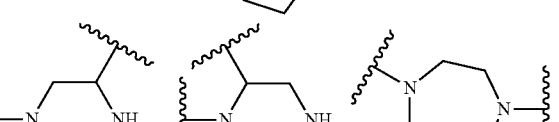

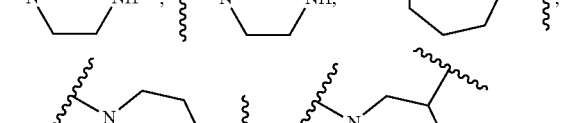

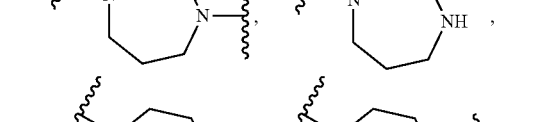

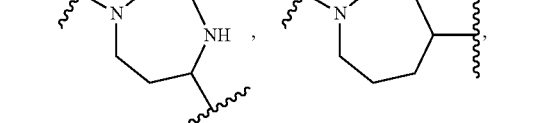

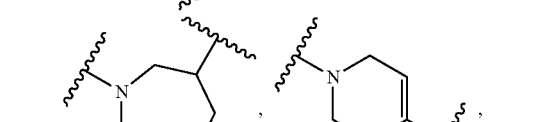

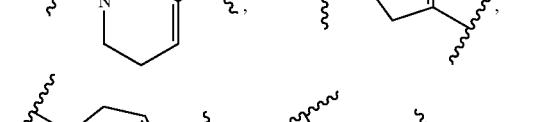, and

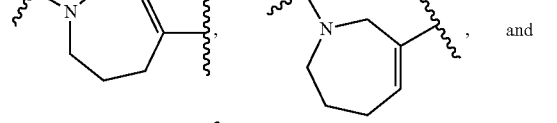

which may optionally be substituted with 1, 2, 3 or 4 substituents independently selected from the group consisting of: methyl, ethyl, n-propyl, isopropyl, n-butyl, sec-butyl, isobutyl, tert-butyl, n-pentyl, sec-pentyl and n-hexyl; or
  a phenylene group, which may be substituted with 1, 2, 3 or 4 substituents independently selected from the group consisting of: F, Cl, Br, —CF$_3$, —OH, —O—CH$_3$, —O—C$_2$H$_5$, —O—CF$_3$, —O—CHF$_2$, —O—CF$_2$H, —S—CF$_3$, —S—CHF$_2$, —S—CF$_2$H, —NO2, methyl, ethyl, n-propyl, isopropyl, n-butyl, sec-butyl, isobutyl and tert-butyl;

D represents a group selected from the group consisting of: phenyl, [1,3,5]-triazinyl, pyridinyl, pyridazinyl, pyrimidinyl, quinolinyl, isoquinolinyl and pyrazinyl, which may optionally be substituted with 1, 2, 3, 4 or 5 substituents independently selected from the group consisting of: F, Cl, Br, —CF$_3$, —OH, —O—CH$_3$, —O—C$_2$H$_5$, —O—CF$_3$, —O—CHF$_2$, —O—CF$_2$H, —S—CF$_3$, —S—CHF$_2$, —S—CF$_2$H, —NO$_2$, methyl, ethyl, n-propyl, isopropyl, n-butyl, sec-butyl, isobutyl, tert-butyl, n-pentyl, sec-pentyl, n-hexyl, —NH—S(=O)$_2$—CH$_3$ and —NH—S(=O)$_2$—C$_2$H$_5$;

E represents a group selected from the group consisting of: —(CH$_2$)—(CH$_2$)—N(R$^7$)—C(=O)—N(R$^8$)—, —(CH$_2$)—(CH$_2$)—N(R$^7$)—C(=S)—N(R$^8$)—, —(CH$_2$)—N(R$^8$)—C(=O)—N(R$^{10}$)—, —(CH$_2$)—N(R$^9$)—C(=S)—N(R$^{10}$)—, —CH=CH—C(=O)—N(R$^{11}$)—, —CH=CH—C(=S)—N(R$^{11}$)—, —(CH$_2$)—(CH$_2$)—N(R$^{12}$)—C(=O)—N(R$^{13}$)—(CH$_2$)—(CH$_2$)—, —(CH$_2$)—(CH$_2$)—N(R$^{12}$)—C(=S)—N(R$^{13}$)—(CH$_2$)—(CH$_2$)—, —(CH$_2$)—N(R$^{14}$)—C(=O)—N(R$^{15}$)—(CH$_2$)—, —(CH$_2$)—N(R$^{14}$)—C(=S)—N(R$^{15}$)—(CH$_2$)—, —N(R$^{16}$)—C(=O)—N(R$^{17}$)—, —N(R$^{16}$)—C(=S)—N(R$^{17}$)—, —(CH$_2$)—N(R$^{18}$)—C(=O)—CH(CH$_3$)—, —(CH$_2$)—N(R$^{18}$)—C(=S)—CH(CH$_3$)—, —C(=O)—N(R$^{19}$)—(CH$_2$)—, —C(=S)—N(R$^{19}$)—(CH$_2$)—, —N(R$^{20}$)—(CH$_2$)—C(=O)—N(R$^{21}$)—, —N(R$^{20}$)—(CH$_2$)—C(=S)—N(R$^{21}$)—, —(CH$_2$)—(CH$_2$)—N(R$^{22}$)—C(=O)—, —(CH$_2$)—(CH$_2$)—N(R$^{22}$)—C(=S)—, —CH(CH$_3$)—N(R$^{23}$)—C(=O)—, —CH(CH$_3$)—N(R$^{23}$)—C(=S)—, —(CH$_2$)—N(R$^{24}$)—C(=O)—N(R$^{25}$)—CH(CH$_3$)— and —(CH$_2$)—N(R$^{24}$)—C(=S)—N(R$^{25}$)—CH(CH$_3$)—;

F represents
a group selected from the group consisting of: quinolinyl, isoquinolinyl, quinoxalinyl, quinazolinyl, (1,4)-benzodioxanyl, (1,3)-benzdioxolyl, (1,2,3,4)-tetrahydronaphthyl, (1,2,3,4)-tetrahydroquinolinyl, (1,2,3,4)-tetrahydroisoquinolinyl, benzoxazolyl, benzothiazolyl, benzisoxazolyl, benzisothiazolyl, benzimidazolyl, 2-oxo-2,3-dihydro-1H-benzimidazolyl, 2-benzoxazolinonyl and 2-benzothiazolinonyl, which may optionally be substituted with 1, 2, 3, 4 or 5 substituents independently selected from the group consisting of: F, Cl, Br, —CF$_3$, —OH, —O—CH$_3$, —O—C$_2$H$_5$, —O—CF$_3$, —O—CHF$_2$, —O—CF$_2$H, —S—CF$_3$, —S—CHF$_2$, —S—CF$_2$H, —NO$_2$, methyl, ethyl, n-propyl, isopropyl, n-butyl, sec-butyl, isobutyl, tert-butyl, n-pentyl, sec-pentyl, n-hexyl, —NH—S(=O)$_2$—CH$_3$ and —NH—S(=O)$_2$—C$_2$H$_5$; or a naphthyl group, which is substituted with 1, 2, 3, 4 or 5 substituents independently selected from the group consisting of: F, Cl, Br, —CF$_3$, —OH, —O—CH$_3$, —O—C$_2$H$_5$, —O—CF$_3$, —O—CHF$_2$, —O—CF$_2$H, —S—CF$_3$, —S—CHF$_2$, —S—CF$_2$H, —NO2, methyl, ethyl, n-propyl, isopropyl, n-butyl, sec-butyl, isobutyl, tert-butyl, n-pentyl, sec-pentyl, n-hexyl, —NH—S(=O)$_2$—CH$_3$ or —NH—S(=O)$_2$-C$_2$H$_5$; or a phenyl group, which is substituted with 2, 3, 4 or 5 substituents, independently selected from the group consisting of F, Cl, Br, —CF$_3$, —OH, —O—CH$_3$, —O—C$_2$H$_5$, —O—CF$_3$, —O—CHF$_2$, —O—CF$_2$H, —S—CF$_3$, —S—CHF$_2$, —S—CF$_2$H, —NO2, methyl, ethyl, n-propyl, isopropyl, n-butyl, sec-butyl, isobutyl, tert-butyl, n-pentyl, sec-pentyl, n-hexyl, —NH—S(=O)$_2$—CH$_3$ or —NH—S(=O)$_2$—C$_2$H$_5$; tetrahydropyridinyl, cyclohexyl, cyclopentyl, cycloheptyl, azepanyl and diazepanyl, which may be substituted with 1, 2, 3 or 4 substituents independently selected from the group consisting of: methyl, ethyl, n-propyl, isopropyl, n-butyl, sec-butyl, isobutyl, tert-butyl, n-pentyl, sec-pentyl, n-hexyl, —NH—CH$_3$, —NH—C$_2$H$_5$, —N(CH$_3$)$_2$ and —N(C$_2$H$_5$)$_2$; or a —NR$^{26}$R$^{27}$—group;

M represents a phenyl group, which may be substituted with 1, 2, 3, 4 or 5 substituents independently selected from the group consisting of —SF$_5$, F, Cl, Br, —CF$_3$, —OH, —O—CH$_3$, —O—C$_2$H$_5$, —O—CF$_3$, —O—CHF$_2$, —O—CF$_2$H, —S—CF$_3$, —S—CHF$_2$, —S—CF$_2$H, —NO$_2$, methyl, ethyl, n-propyl, isopropyl, n-butyl, sec-butyl, isobutyl and tert-butyl and/or can be bound via a —O—CH$_2$—, —S—CH$_2$—, —CH$_2$—CH$_2$—, —CH=CH— or —CH$_2$-group;

R$^3$, R$^4$, R$^5$, R$^6$, R$^7$, R$_8$, R$^9$, R$^{10}$, R$^{11}$, R$^{12}$, R$^{13}$, R$^{14}$, R$^{15}$, R$^{16}$, R$^{17}$, R$_{18}$, R$^{19}$, R$^{20}$, R$^{21}$, R$^{22}$, R$^{23}$, R$^{24}$ and R$^{25}$ each independently represent hydrogen or a group selected from the group consisting of: methyl, ethyl, n-propyl, isopropyl, n-butyl, sec-butyl, isobutyl, tert-butyl, n-pentyl, sec-pentyl and n-hexyl; and R$^{26}$ and R$^{27}$ each independently represent a group selected from the group consisting of: hydrogen, methyl, ethyl, n-propyl, isopropyl, n-butyl, sec-butyl, isobutyl, tert-butyl, n-pentyl, sec-pentyl and n-hexyl;

or a salt thereof.

2. A compound according to claim 1, wherein said compound is in the form of an isolated or purified stereoisomer.

3. A compound according to claim 1, wherein said compound is in the form of a mixture of stereoisomers in any mixing ratio.

4. A compound according to claim 3, wherein said compound is in the form of a racemic mixture.

5. A compound according to claim 1, wherein n is 0.

6. A compound according to claim 1, wherein R$^2$ denotes
a group -A-B-D, -E-F or —N(H)-G, which is bound to position 4 of the phenyl group of formula I, or
a group -Q-B-D; wherein Q represents a group selected from the group consisting of: oxazolyl, thiazolyl, isoxazolyl, isothiazolyl and imidazolyl, which is condensed with the phenyl group of formula I in positions 4 and 5 and therefore forms a optionally substituted group selected from the group consisting of: benzoxazolyl, benzothiazolyl, benzisothiazolyl and benzimidazolyl.

7. A compound according to claim 1, wherein B represents a group selected from the group consisting of:

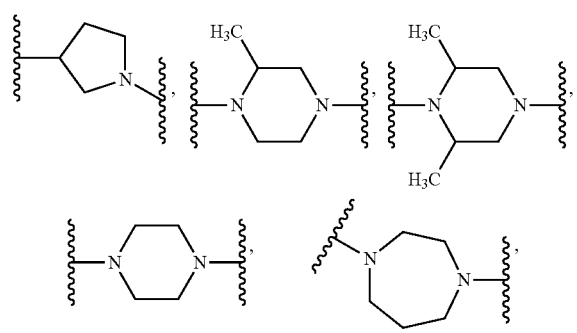

-continued

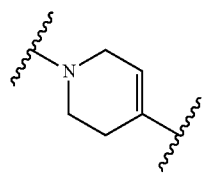 and 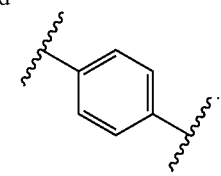.

8. A compound according to claim 1, wherein D represents a group selected from the group consisting of:
G represents a group selected from the group consisting of:

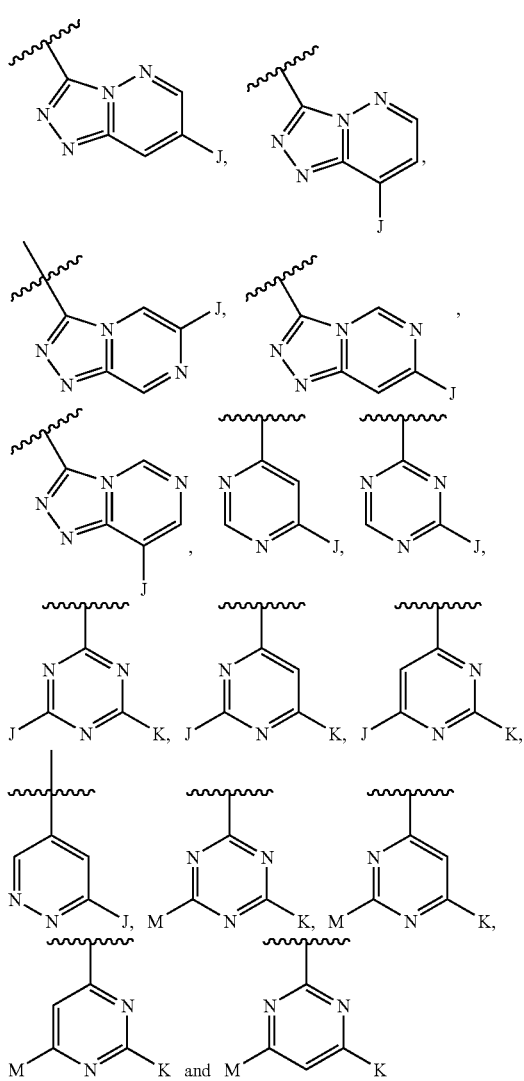

J represents a group selected from the group consisting of phenyl, [1,3,5]-triazinyl, pyridinyl, pyrimidinyl, pyridazinyl, quinolinyl, isoquinolinyl and pyrazinyl, which may optionally be substituted with 1, 2, 3, 4 or 5 substituents independently selected from the group consisting of: F, Cl, Br, —$CF_3$, —OH, —O—$CH_3$, —O—$C_2H_5$, —O—$CF_3$, —O—$CHF_2$, —O—$CF_2H$, —S—$CF_3$, —S—$CHF_2$, —S—$CF_2H$, —NO2, methyl, ethyl, n-propyl, isopropyl, n-butyl, sec-butyl, isobutyl, tert-butyl, n-pentyl, sec-pentyl, n-hexyl, —NH—S(=O)$_2$—$CH_3$ and —NH—S(=O)$_2$—$C_2H_5$;

K represents a group selected from the group consisting of: piperidinyl, piperazinyl, pyrrolidinyl, morpholinyl, thiomorpholinyl, (1,2,3,6)-

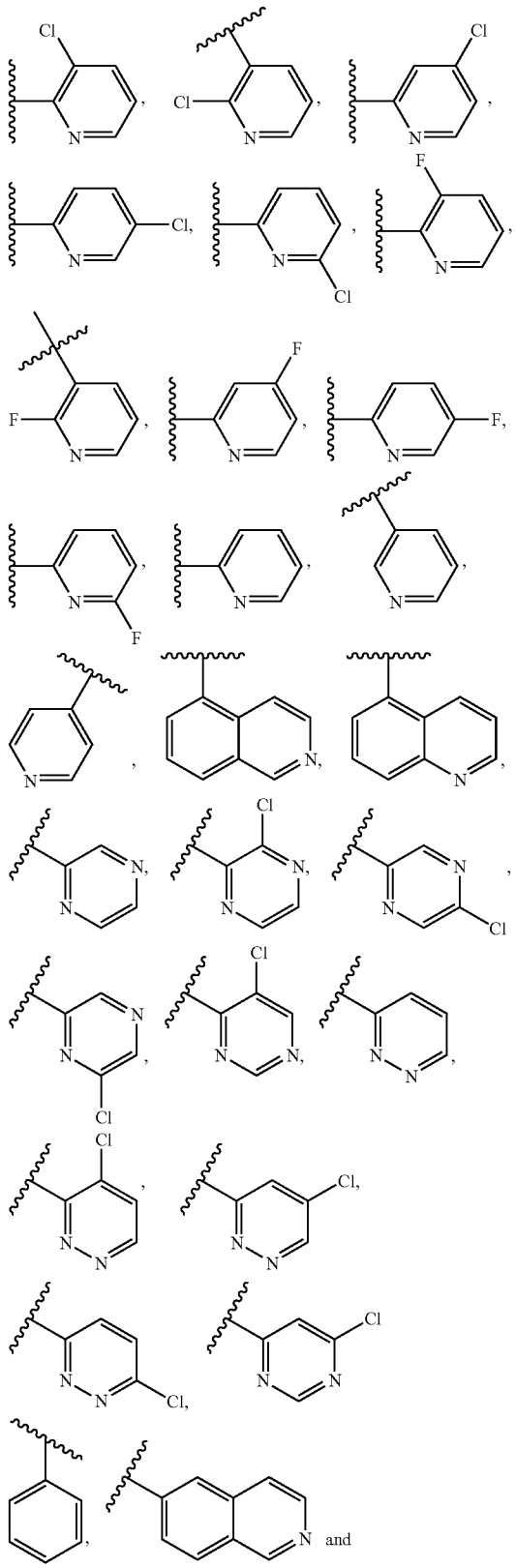

9. A compound according to claim 1, wherein F represents a group selected from the group consisting of: [structures shown]

10. A compound according to claim 1, wherein J represents a group selected from the group consisting of: [structures shown]

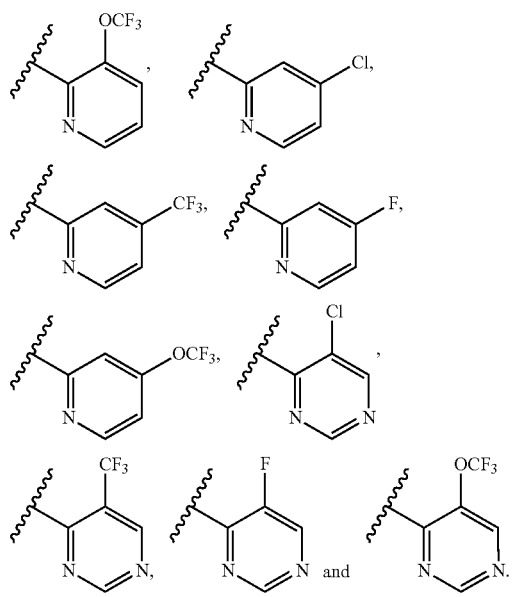

11. A compound according to claim 1, wherein K represents a group selected from the group consisting of:

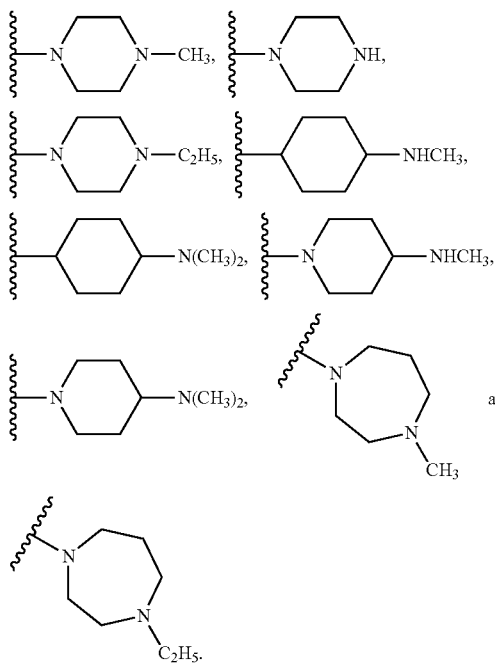

12. A compound according claim 1, wherein M represents a group selected from the group consisting of:

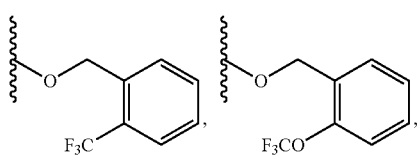

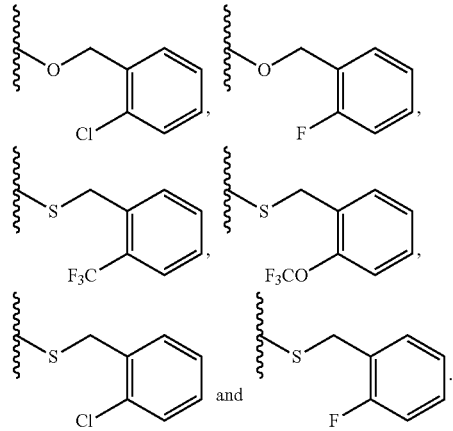

13. A compound according to claim 1, wherein n is 0,

R² represents a group -A-B-D, -E-F or —N(H)-G, which can be bound to position 4 of the phenyl group of formula I; or a group -Q-B-D; wherein Q represents a group selected from the group consisting of: oxazolyl, thiazolyl, isoxazolyl, isothiazolyl and imidazolyl, which is condensed with the phenyl group of formula I in positions 4 and 5 and thereby forms an optionally substituted group selected from the group consisting of: benzoxazolyl, benzothiazolyl, benzisothiazolyl and benzimidazolyl;

A represents a group selected from the group consisting of:
—N(R³)—C(=O)—N(R⁴)—, —N(R³)—C(=S)—N(R⁴)—, —N(R⁵)—C(=O)—, —N(R⁵)—C(=S)—,

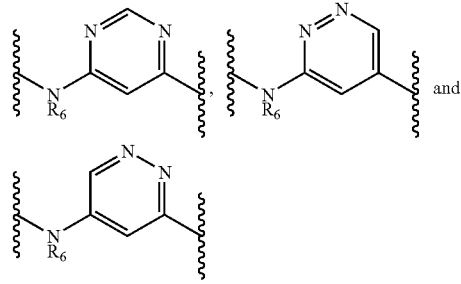

B represents a group selected from the group consisting of:

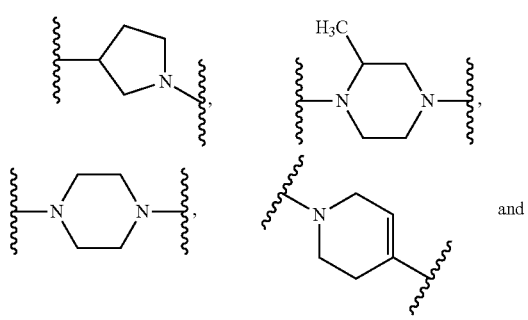

-continued

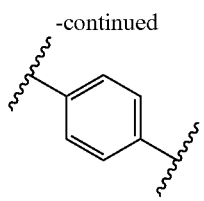

D represents a group selected from the group consisting of:

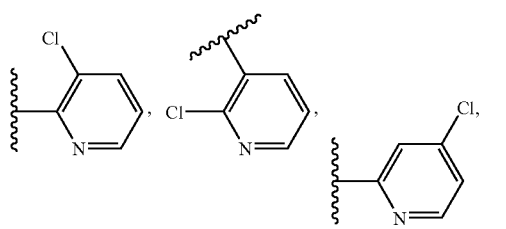

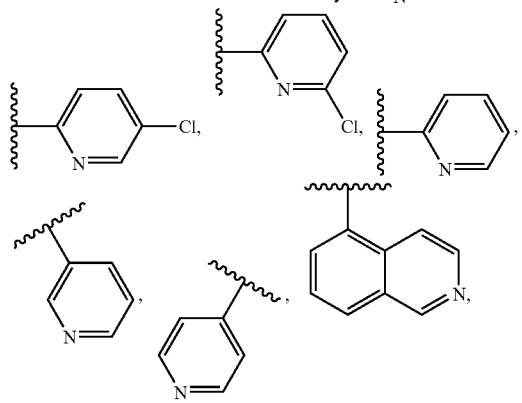

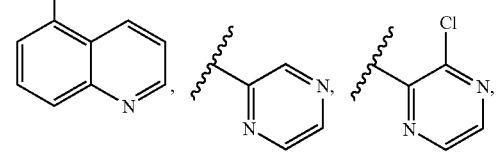

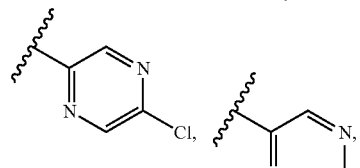

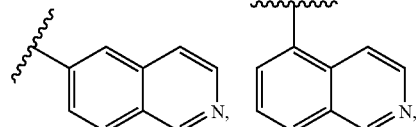 and 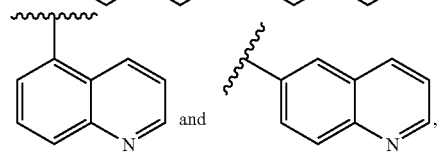

E represents a group selected from the group consisting of:
—(CH$_2$)—(CH$_2$)—N(R$^7$)—C(=O)—N(R$^8$)—,
—(CH$_2$)—(CH$_2$)—N(R$^7$)—C(=S)—N(R$^8$)—,
—(CH$_2$)—N(R$^9$)—C(=O)—N(R$^{10}$)—, —(CH$_2$)—N(R$^9$)—C(=S)—N(R$^{10}$)—, —CH=CH—C(=O)—N(R$^{11}$)—, —CH=CH—C(=S)—N(R$^{11}$)—, —(CH$_2$)—(CH$_2$)—N(R$^{12}$)—C(=O)—N(R$^{13}$)—(CH$_2$)—(CH$_2$)—, —(C$_2$)—(CH$_2$)—N(R$^{12}$)—C(=S)—N(R$^{13}$)—(CH$_2$)—(CH$_2$)—, —(CH$_2$)—N(R$^{14}$)—C(=O)—N(R$^{15}$)—(CH$_2$)—, —(CH$_2$)—N(R$^{14}$)—C(=S)—N(R$^{15}$)—(CH$_2$)—, —N(R$^{16}$)—C(=O)—N(R$^{17}$)—, —N(R$^{16}$)—C(=S)—N(R$^{17}$)—, —(CH$_2$)—N(R$^{18}$)—C(=O)—CH(CH$_3$)—, —(CH$_2$)—N(R$^{18}$)—C(=S)—CH(CH$_3$)—, —C(=O)—N(R$^{19}$)—(CH$_2$)—, —C(=S)—N(R$^{19}$)—(CH$_2$)—, —N(R$^{20}$)—(CH$_2$)—C(=O)—N(R$^{21}$)—, —N(R$^{20}$)—(CH$_2$)—C(=S)—N(R$^{21}$)—, —(CH$_2$)—(CH$_2$)—N(R$^{22}$)—C(=O)—, —(CH$_2$)—(CH$_2$)—N(R$^{22}$)—C(=S)—, —CH(CH$_3$)—N(R$^{23}$)—C(=O)—, —CH(CH$_3$)—N(R$^{23}$)—C(=S)—, —(CH$_2$)—N(R$^{24}$)—C(=O)—N(R$^{25}$)—CH(CH$_3$)—, and —(CH$_2$)—N(R$^{24}$)—C(=S)—N(R$^{25}$)—CH(CH$_3$)—;

F represents a group selected from the group consisting of:

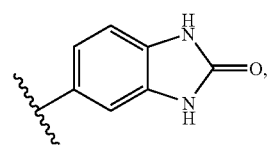

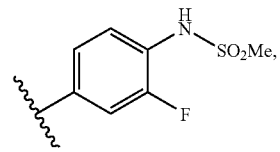

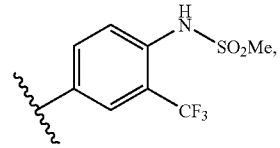

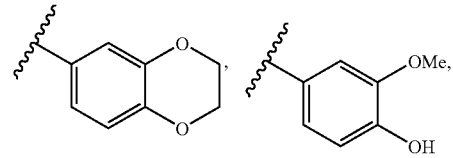

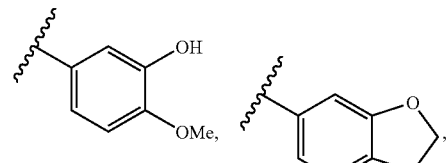

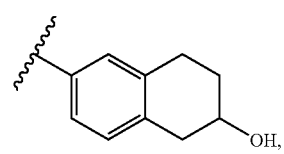

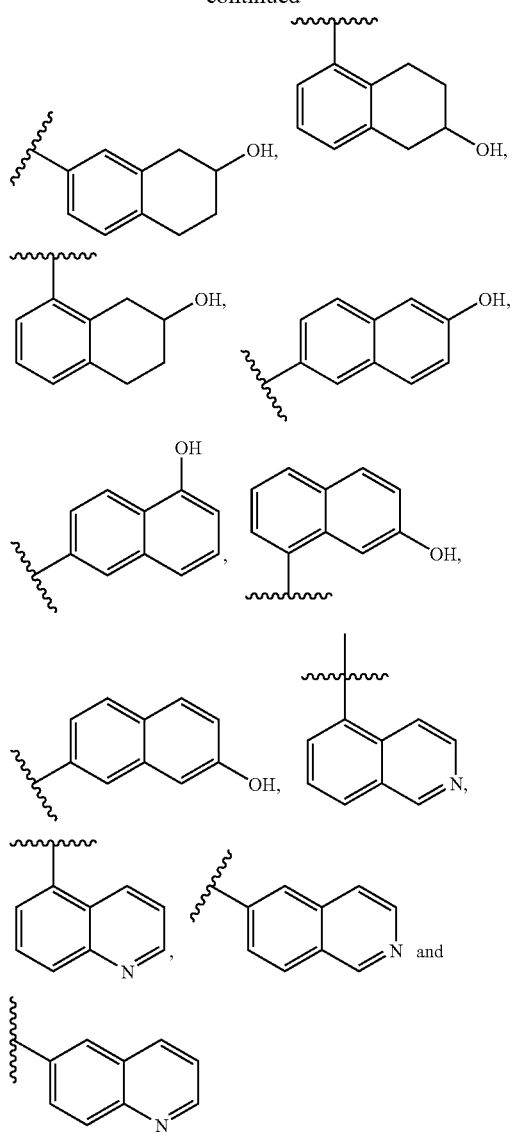
G represents a group selected from the group consisting of:
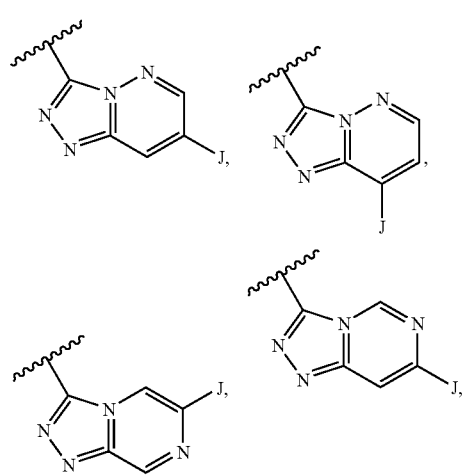
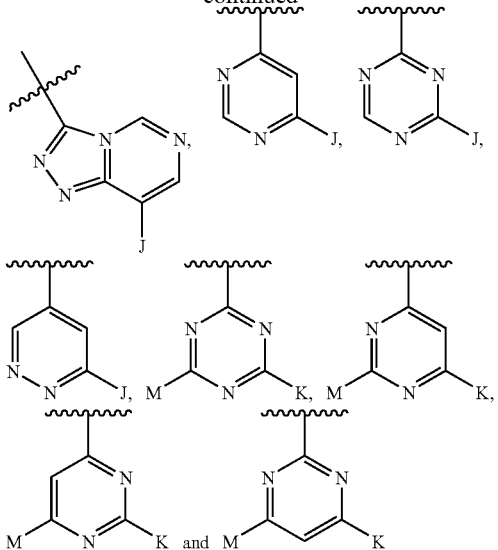
J represents a group selected from the group consisting of:
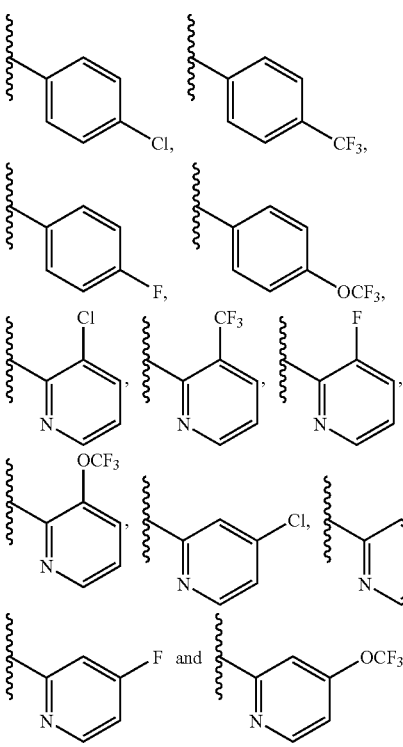
K represents a group selected from the group consisting of:
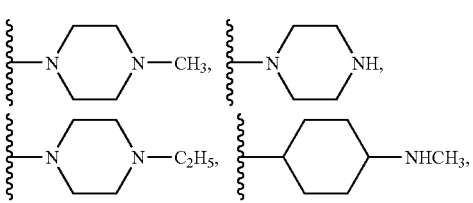

-continued

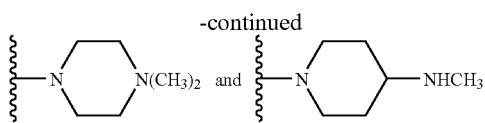

M represents a group selected from the group consisting of:

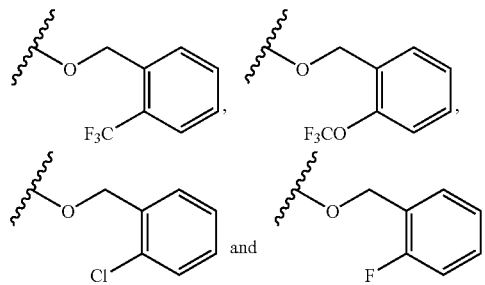

and
$R^3, R^4, R^5, R^6, R^7, R^8, R^9, R^{10}, R^{11}, R^{12}, R^{13}, R^{14}, R^{15}, R^{16}, R^{17}, R^{18}, R^{19}, R^{20}, R^{21}, R^{22}, R^{23}, R^{24}$ and $R^{25}$ each represent hydrogen.

14. A compound according to claim 1, selected from the group consisting of:

[1] N-{4-[3-(4-pentafluorosulphanyl-benzyl)-thioureidomethyl]-2-fluoro-phenyl}-methane sulphonamide;
[2] 4-(3-chloropyridin-2-yl)-piperazine-1-carboxy-(4-pentafluorosulphanyl-phenyl)-amide;
[3] 4-(3-chloro-pyridin-2-yl)-piperazine-l-thiocarboxy-(4-pentafluorosulphanyl-phenyl)-amide;
[4] 3-(4-pentafluorosulphanyl-phenyl)-N-(2,3-dihydro-benzo[1,4]dioxin-6-yl)-acrylamide;
[5] N-(4-pentafluorosulphanyl-benzyl)-2-(3-fluor-4-methanesulphonylamino-phenyl)-propionamide;
[6] (2R)-N-(4-pentafluorosulphanyl-benzyl)-2-(3-fluoro-4-methansulphonylamino-phenyl)-propionamide;
[7] (2S)-N-(4-pentafluorosulphanyl-benzyl)-2-(3-fluoro-4-methanesulphonylamino-phenyl)-propionamide;
[8] N-(4-pentafluorosulphanyl-phenyl)-4-pyridin-2-yl-benzamide [9] 1-(4-pentafluorosulphanyl-benzyl)-3-(7-hydroxy-naphthalen-1-yl)-urea;
[10] 4-(3-chloro-pyrazin-2-yl)-3,6-dihydro-2H-pyridine-1-carboxy-(4-pentafluorosulphanyl -phenyl)-amide;
[11] (4-pentafluorosulphanyl-phenyl)-[4-(4-methyl-piperazin-l-yl)-6-(2-trifluoromethyl -benzyloxy)-[1,3,5]triazin-2-yl]-amine;
[12] (4-pentafluorosulphanyll-phenyl)-[6-(4-chloro-phenyl)-pyrimidin-4-yl]-amine;
[13] 4-pentafluorosulphanyl-N-(2-oxo-2,3-dihydro-1H-benzoimidazol-5-ylmethyl) -benzamide,
[14] (4-pentafluorosulphanyl-phenyl)-{6-[4-(3-chloro-pyridin-2-yl)-2-(R)-methyl-piperazin -1-yl]-pyrimidin-4-yl}-amine;
[15] 3'-chloro-3,6-dihydro-2H-[1,2']bipyridinyl-4-carboxy-(4-pentafluorosulphanyl -phenyl)-amide;
[16] 2-(4-pentafluorosulphanyl-phenylamino)-N-(7-hydroxy-naphthalen-l-yl)-acetamide;
[17] (4-pentafluorosulphanyl-phenyl)[7-(3-trifluoromethyl-pyridin-2-yl)-[1,2,4]triazolo[4,3-bipyridazin-3-yl]-amine;
[18] 1-(4-pentafluorosulphanyl-benzyl) -3-isoquinolin-5-yl-urea;
[19] 1- [2-(4-pentafluorosulphanyl-phenyl)-ethyl] -3-isoquinolin-5-yl-urea;
[20] 1-(4-pentafluorosulphanyl-phenyl)-3-(7-hydroxy-5,6,7,8-tetrahydro -naphthalen-1-yl)-urea;
[21] 1- [2-(4-pentafluorosulphanyl-phenyl)-ethyl]-3-quinolin-5-yl-urea;
[22] 1-(4-pentafluorosulphanyl-phenyl)-3-(1-isoquinolin-5-yl-pyrrolidin-3-yl)-urea;
[23] 5-pentafluorosulphanyl-2-[4-(3-chloro-pyridin-2-yl)-piperazin-1-yl]-benzooxazole; and
[24] N-{4-[3-(4-pentafluorosulphanyl-benzyl)-ureidomethyl]-2-fluoro-phenyl}-methanesulphonamide.

15. A process for producing a compounds of formula I according to claim 1, said process comprising reacting a compound of formula II

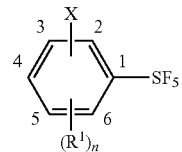

wherein $R^1$ and n have the meanings given in claim 1, and
X represents —N=C=O, —N=C=S, —(CH$_2$)—N=C=O, —(CH$_2$)—N=C=S, —(CH$_2$)—(CH$_2$)—N=C=O, —(CH$_2$)—(CH$_2$)—N=C=S, —CH(CH$_3$)—N=C=O or —CH(CH$_3$)—N=C=S,
in a reaction medium in the presence of a base,
with a compound of formula H-B-D; wherein the group H-B has at least one —N(H)-group, H$_2$N-B-D, H$_2$N—F, H$_2$N—(CH$_2$)—F, H$_2$N—(CH$_2$)—(CH$_2$)—F or H$_2$N—CH(CH$_3$)—F; wherein B, D and F have the meanings given in claim 1; or
reacting a compound of formula II, wherein
$R^1$ and n have the meanings given in claim 1, and
X represents —NH$_2$, —(CH$_2$)—NH$_2$, —CH(CH$_3$)—NH$_2$ or —(CH$_2$)—(CH$_2$)—NH$_2$,
in a reaction medium in the presence of a base,
with a compound of formula F—N=C=O, F—N=C=S, F—(CH$_2$)—N=C=O, F—(CH$_2$)—N=C=S, F—(CH)$_2$—(CH$_2$)—N=C=O, F—(CH$_2$)—(CH$_2$)—N=C=S, F—CH(CH$_3$)—N=C=O or F—CH(CH$_3$)—N=C=S; wherein F has the meaning given above;
to obtain a compound of formula I; wherein
$R^1$ and n have the meanings given above, and
$R^2$ represents -A-B-D or -E-F, wherein
A represents —N(R$^3$)—C(=O)—N(R$^4$)—or —N(R$^3$)—C(=S)—N(R$^4$)—;
E represents a group selected from the group consisting of:
—(CH$_2$)—(CH$_2$)—N(R$^7$)—C(=O)—N(R$^8$)—,
—(CH$_2$)—(CH$_2$)—N(R$^7$)—C(=S)—N(R$^8$)—,
—(CH$_2$)—N(R$^9$)—C(=O)—N(R$^{10}$)—, —(CH$_2$)—N(R$^9$)—C(=S)—N(R$^{10}$)—, —(CH$_2$)—(CH$_2$)—N(R$^{12}$)—C(=O)—N(R$^{13}$)—(CH$_2$)—(CH$_2$)—,
—(CH$_2$)—(CH$_2$)—N(R$^{12}$)—C(=S)—N(R$^{13}$)—(CH$_2$)—(CH$_2$)—, —(CH$_2$)—N(R$^{14}$)—C(=O)—N(R$^{15}$)—(CH$_2$)—, —(CH$_2$)—N(R$^{14}$)—C(=S)—N(R$^{15}$)—(CH$_2$)—, —N(R$^{16}$)—C(=O)—N(R$^{17}$)—, —N(R$^{16}$)—C(=S)—N(R$^{17}$)—, —(CH$_2$)—N(R$^{24}$)—C(=O)—N(R$^{25}$)—CH(CH$_3$)—and —(CH$_2$)—N(R$^{24}$)—C(=S)—N(R$^{25}$)—CH(CH$_3$)—; wherein R$^3$, R$^4$, R$^7$, R$^8$, R$^{13}$, R$^{14}$, R$^{15}$, R$^{16}$, R$^{17}$, R$^{24}$ and R$^{25}$ each represent hydrogen; and B, D and F have the meanings given above; and
optionally reacting a compound of formula I; wherein
$R^1$ and n have the meanings given above; and
$R^2$ represents -A-B-D or -E-F, wherein
A represents —N($R^3$)—C(=O)—N($R^4$)— or —N($R^3$)—C(=S)—N($R^4$)—;
E represents a group selected from the group consisting of:
—(CH$_2$)—(CH$_2$)—N($R^7$)—C(=O)—N($R^8$)—,
—(CH$_2$)—(CH$_2$)—N($R^7$)—C(=S)—N($R^8$)—,
—(CH$_2$)—N($R^9$)—C(=O)—N($R^{10}$)—, —(CH$_2$)—N($R^9$)—C(=S)—N($R^{10}$)—, —(CH$_2$)—(CH$_2$)—N($R^{12}$)—C(=O)—N($R^{13}$)—(CH$_2$)—(CH$_2$)—,
—(CH$_2$)—(CH$_2$)—N($R^{12}$)—C(=S)—N($R^{13}$)—(CH$_2$)—(CH$_2$)—, —(CH$_2$)—N($R^{14}$)—C(=O)—N($R^{15}$)—(CH$_2$)—, —(CH$_2$)—N($R^{14}$)—C(=S)—N($R^{15}$)—(CH$_2$)—, —N($R^{16}$)—C(=O )—N($R^{17}$)—, —N($R^{16}$)—C(=S)—N($R^{17}$)—, —(CH$_2$)—N($R^{24}$)—C(=O)—N($R^{25}$)—CH(CH$_3$)— and —(CH$_2$)—N($R^{24}$)—C(=S)—N($R^{25}$)—CH(CH$_3$)—; wherein $R^3$, $R^4$, $R^7$, $R^8$, $R^9$, $R^{10}$, $R^{11}$, $R^{12}$, $R^{13}$, $R^{14}$, $R^{15}$, $R^{16}$, $R^{17}$, $R^{24}$ and $R^{25}$ each represent hydrogen; and
B, D and F have the meanings given in claim 1;
in a reaction medium, in the presence of a base,
with a compound of the formula LG-$R^3$, LG-$R^4$, LG-$R^7$, LG-$R^8$, LG-$R^9$, LG-$R^{10}$, LG $R^{12}$, LG-$R^{13}$, LG-$R^{14}$, LG-$R^{15}$, LG-$R^{16}$, LG-$R^{17}$, LG-$R^{24}$ or LG-$R^{25}$; wherein $R^3$, $R^4$, $R^7$, $R^8$, $R^9$, $R^{10}$, $R^{12}$, $R^{13}$, $R^{14}$, $R^{15}$, $R^{16}$, $R^{17}$, $R^{24}$ and $R^{25}$ have the meanings given in claim 22, with the exception of hydrogen and LG denotes a leaving group;
to obtain a compound of formula I, wherein
$R^1$ and n have the meanings given above; and
$R^2$ represents -A-B-D or -E-F, wherein
A represents —N($R^3$)—C(=O)—N($R^4$)— or —N($R^3$)—C(=S)—N($R^4$)—;
E represents a group selected from the group consisting of:
—(CH$_2$)—(CH$_2$)—N($R^7$)—C(=O)—N($R^8$)—,
—(CH$_2$)—(CH$_2$)—N($R^7$)—C(=S)—N($R^8$)—,
—(CH$_2$)—N($R^9$)—C(=O )—N($R^{10}$)—, —(CH$_2$)—N($R^9$)—C(=S)—N($R^{10}$)—, —(CH$_2$)—(C$_2$)—N($R^{12}$)—C(=O)—N($R^{13}$)—(CH$_2$)—(CH$_2$)—, —(CH$^2$)—(CH$_2$)—N($R^{12}$)—C(=S)—N($R^{13}$)—(CH$_2$)—(C$_2$)—,
—(CH$_2$)—N($R^{14}$)—C(=O)—N($R^{15}$)—(CH$_2$)—,
—(C$_2$)—N($R^{14}$)—C(=S)—N($R^{15}$)—(CH$_2$)—,
—N($R^{16}$)—C(=O)—N($R^{17}$)—, —N($R^{16}$)—C(=S)—N($R^{17}$)—, —(CH$_2$)—N($R^{24}$)—C(=O)—N($R^{25}$)—CH(CH$_3$)— and —(CH$_2$)—N($R^{24}$)—C(=S)—N($R^{25}$)—CH(CH$_3$)—; wherein $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{24}$ and $R^{25}$ have the meanings given in claim 1 with the exception of hydrogen; and
B, D and F have the meanings given in claim 1;
and optionally isolating or purifying any of the obtained compounds.

16. A process for producing a compound of formula I according to claim 1, said process comprising:
reacting a compound of formula II

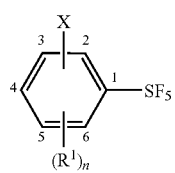

wherein
$R^1$ and n have the meanings given in claim 1, and
X represents —NH$_2$,
in a reaction medium
with a compound of the formula LG-G, wherein
G has the meaning given in claim 1, and
LG denotes a leaving group and
to obtain a compound of formula I, wherein
$R^1$ and n have the meanings given above, and
$R^2$ represents —N(H)-G, wherein G has the meaning given above;
and optionally isolating or purifying the obtained compound.

17. A process for producing a compound of formula I according to claim 1, said process comprising:
reacting a compound of formula III

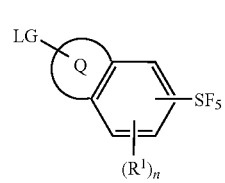

wherein
$R^1$, n and Q have the meanings given in claim 1, and
LG denotes a leaving group,
in a reaction medium,
with a compound of formula H-B-D; wherein the group H-B has at least one —N(H)-group and B and D have the meanings given in claim 1,
to obtain a compound of formula I, wherein
$R^1$ and n have the meanings given above, and
$R^2$ represents -Q-B-D, wherein Q, B and D have the meanings given above;
and optionally isolating or purifying the obtained compound.

18. A process for producing a compound of formula I according to claim 1, said process comprising:
reacting a compound of formula II

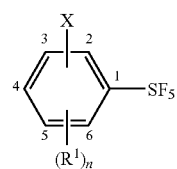

wherein
$R^1$ and n have the meanings given in claim 1, and
X represents —C(=O)—LG, —(CH$_2$)—C(=O)—LG, —(CH$_2$)—(CH$_2$)—C(=O)—LG, —CH(CH$_3$)—C(=O)—LG, —CH=CH—C(=O)—LG or —N($R^{20}$)—CH$_2$—C(=O)—LG, wherein LG denotes a leaving group and $R^{20}$ has the meaning given in claim 1,
in a reaction medium in the presence of a base,
with at least one compound of formula H-B-D; wherein the group H-B has at least one —N(H)— group, H$_2$N-B-D, H$_2$N-F, H$_2$N—(CH$_2$)—F, H$_2$N—(CH$_2$)—(CH$_2$)—F or H$_2$N—CH(CH$_3$)—F; wherein B, D and F have the meanings given in claim 1; or reacting a compound of formula II, wherein
R¹ and n have the meanings given in claim 1, and
X represents —NH₂, —(CH₂)—NH₂, —CH(CH₃)—NH₂, —(CH₂)—(CH₂)—NH₂ or —CH=CH—NH₂,
in a reaction medium, in the presence of a base,
with a compound of formula F—C(=O)—LG, F—(CH₂)—C(=O)—LG, F—(CH₂)—(CH₂)—C(=O)—LG, F—CH(CH₃)—C(=O)—LG, F—CH=CH—C(=O)—LG or F—N(R²⁰)—CH₂—C(=O)-LG; wherein F, R²⁰ and LG have the meanings given above;
to obtain a compound of formula I, wherein
R¹ and n have the meanings given above, and
R² represents -A-B-D or -E-F, wherein
A represents —N(R⁵)—C(=O)—;
E represents a group selected from the group consisting of: —CH=CH—C(=O —N(R¹¹), —(CH₂)—N(R¹⁸)—C(=O)—CH(CH₃)—, —C(=O)—N(R¹⁹)—(CH₂)—, —N(R²⁰)—(CH₂)—C(=O)—N(R²¹)—, —(CH₂)—(CH₂)—N(R²²)—C(=O)— and —CH(CH₃)—N(R²³)—C(=O)—; wherein R⁵, R¹¹, R¹⁸, R¹⁹, R²⁰, R²¹, R²² and R²³ each represent a hydrogen group; and
B, D and F have the meanings given in claim 1; and
optionally reacting a compound of formula I, wherein
R¹ and n have the meanings given above, and
R² represents -A-B-D or -E-F, wherein
A represents —N(R⁵)—C(=O)—;
E represents a group selected from the group consisting of —CH=CH—C(=O) —N(R¹¹), —(CH₂)—N(R¹⁸)—C(=O)—CH(CH₃)—, —C(=O)—N(R¹⁹)—(CH₂)—, —N(R²⁰)—(CH₂)—C(=O)—N(R²¹)—, —(CH₂)—(CH₂)—N(R²²)—C(=O)— and —CH(CH₃)—N(R²³)—C(=O)—; wherein R⁵, R¹¹, R¹⁸, R¹⁹, R²⁰, R²¹, R²² and R²³ each represent a hydrogen group; and
B, D and F have the meanings given in claim 1;
in a reaction medium in the presence of a base,
with a compound of formula LG-R⁵, LG-R¹¹, LG-R¹⁸, LG-R¹⁹, LG-R²⁰, LG-R²¹, LG-R²² or LG-R²³, wherein R⁵, R₁₁, R₁₈, R¹⁹, R²⁰, R²¹, R²² and R²³ have the meanings given in claim 1 with the exception of hydrogen,
to obtain a compound of formula I, wherein
R¹ and n have the meanings given above, and
R² represents -A-B-D or -E-F, wherein
A represents —N(R⁵)—C(=O)—;
E represents a group selected from the group consisting of: —CH=CH—C(=O) —(CH₂)—N(R¹⁸)—C(=O)—CH(CH₃)—, —C(=O)—N(R¹⁹)—(CH₂)—, —N(R²⁰)—(CH₂)—C(=O)—N(R²¹)—, —(CH₂)—(CH₂)—N(R²²)—C(=O)— and —CH(CH₃)—N(R²³)—C(=O)—; wherein R⁵, R¹¹, R¹⁸, R¹⁹, R²⁰, R²¹, R²² and R²³ have the meanings given in claim 1; and
B, D and F have the meanings given in claim 1; and
optionally reacting a compound of formula I, wherein
R¹ and n have the meanings given above, and
R² represents -A-B-D or -E-F, wherein
A represents —N(R⁵)—C(=O)—;
E represents a group selected from the group consisting of: —CH=CH—C(=O) —N(R¹¹), —(CH₂)—N(R¹⁸)—C(=O)—CH(CH₃)—, —C(=O)—N(R¹⁹)—(CH₂)—, —N(R²⁰) —(CH₂)—C(=O)—N(R²¹)—, —(CH₂)—(CH₂)—N(R²²)—C(=O)— and —CH(CH₃)—N(R²³)—C(=O)—; wherein R⁵, R¹¹, R¹⁸, R¹⁹, R²⁰, R²¹, R²² and R²³ have the meanings given in claim 1; and B, D and F have the meanings given in claim 1,
in a reaction medium,
with a compound of formula IV

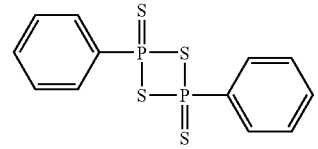

IV wherein the phenyl groups optionally may be substituted with 1 or 2 substituents independently selected from the group consisting of: methoxy, phenoxy, Cl, methyl and Br, or with phosphorus pentasulphide,
to obtain a compound of formula I, wherein
R¹ and n have the meanings given above, and
R² represents -A-B-D or -E-F, wherein
A represents —N(R⁵)—C(=S)—;
E represents a group selected from the group consisting of: —CH=CH—C(=S) —N(R¹¹), —(CH₂)—N(R¹⁸)—C(=S)—CH(CH₃)—, —C(=S)—N(R¹⁹)—(CH₂)—, —N(R²⁰)—(CH₂)—C(=S)—N(R²¹)—, —(CH₂)—(CH₂)—N(R²²)—C(=S)— and —CH(CH₃)—N(R²³)—C(=S)—;
wherein R⁵, R¹¹, R¹⁸, R¹⁹, R²⁰, R²¹, R²² and R²³ d have the meanings given in claim 1; and
B, D and F have the meanings given in claim 1;
and optionally isolating or purifying any of the obtained compounds.

19. A process for producing a compound of formula I according to claim 1; said process comprising:
reacting a compound of formula II

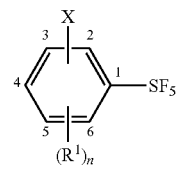

II wherein
R¹ and n have the meanings given in claim 1, and
X represents —NH₂ or —NHR⁶; wherein R⁶ has the meaning given in claim 1,
in a reaction medium,
with a compound of formula A-B-D, wherein
B and D have the meanings given in claim 1, and
A represents a group selected from the group consisting of:

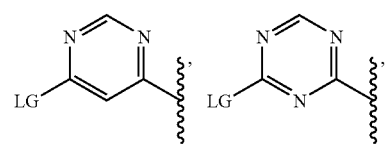

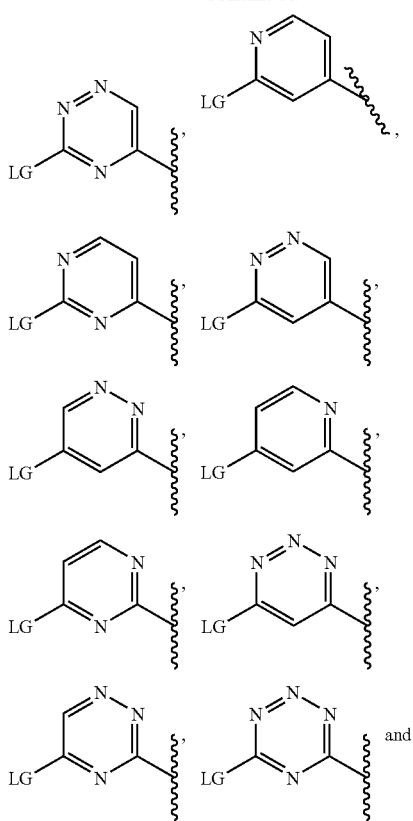

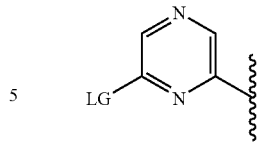

wherein LG denotes a leaving group,
in a reaction medium,
to obtain a compound of formula I, wherein
$R^1$, $R^6$ and n have the meanings given above, and
$R^2$ represents -A-B-D, wherein
B and D have the meanings given above, and
A has the meaning given in claim 1 with the exception of —N($R^3$)—C(=O)—N($R^4$)—, —N($R^3$)—C(=S)—N($R^4$)—, —N($R^5$)—C(=O)— and —N($R^5$)—C(=S)—;
and optionally isolating or purifying the obtained compound.

20. A pharmaceutical composition comprising a compound according to claim 1 and at least one physiologically compatible excipient.

21. A method of treating a disorder or disease state mediated via the transient receptor potential vanilloid receptor 1 (TRPV1) and selected from the group consisting of pain; migraine; urinary incontinence; obesity; anxiety; and epilepsy in a subject suffering therefrom, said method comprising administering to said subject a pharmacologically effective amount of a TRPV1 receptor binding compound according to claim 1.

22. A method according to claim 21, wherein said disorder or disease state is pain selected from the group consisting of acute pain, chronic pain, neuropathic pain and visceral pain.

* * * * *